US007482016B2

(12) United States Patent
Doerr et al.

(10) Patent No.: US 7,482,016 B2
(45) Date of Patent: Jan. 27, 2009

(54) IMMUNOGENIC COMPOSITIONS COMPRISING HIV-1 ACETYLATED TAT POLYPEPTIDES

(75) Inventors: Alexander P. Doerr, Geneva (CH); Melanie Ott, San Francisco, CA (US); Eric Verdin, San Francisco, CA (US)

(73) Assignees: The J. David Gladstone Institutes, San Francisco, CA (US); Deutsches Krebsforschungszentrum, Heidelberg (DE)

( * ) Notice: Subject to any disclaimer, the term of this patent is extended or adjusted under 35 U.S.C. 154(b) by 596 days.

(21) Appl. No.: 10/799,854

(22) Filed: Mar. 12, 2004

(65) Prior Publication Data

US 2004/0247614 A1 Dec. 9, 2004

Related U.S. Application Data

(60) Provisional application No. 60/456,468, filed on Mar. 19, 2003.

(51) Int. Cl.
*A61K 39/21* (2006.01)
*A61K 39/385* (2006.01)

(52) U.S. Cl. ............... 424/208.1; 424/188.1; 424/193.1

(58) Field of Classification Search .............. 424/188.1, 424/208.1, 193.1
See application file for complete search history.

(56) References Cited

U.S. PATENT DOCUMENTS

| 5,891,994 | A | 4/1999 | Goldstein | |
|---|---|---|---|---|
| 6,419,931 | B1 * | 7/2002 | Vitiello et al. | ........... 424/201.1 |
| 6,447,778 | B1 * | 9/2002 | Rubinstein et al. | ....... 424/188.1 |
| 2002/0001589 | A1 * | 1/2002 | Gu et al. | .................. 424/184.1 |
| 2006/0051360 | A1 | 3/2006 | Nath et al. | |

OTHER PUBLICATIONS

Deng, L., et al., 2000, Acetylation of HIV-1 Tat by CBP/P300 increases transcription of integrated HIV-1 genome and enhances binding to core histones, Virol. 277:278-295.*
Mujtaba, S., et al., 2002, Structural basis of lysine-acetylated HIV-1 Tat recognition by PCAF bromodomain, Mol. Cell 9:575-586.*
Deng, L., et al., 2000, "Acetylation of HIV-1 Tat by CBP/P300 increases transcription of integrated HIV-1 genome and enhances binding to core histones", Virol. 277:278-295.*
Yasuhiko, K., et al., 2003, "Four different clones of mouse anti-acetyllysine monoclonal antibodies having different recognition properties share a common immunoglobulin framework structure", J. Immunol. Methods 272(1-2):161-75 (abstract provided).*
Frankel, A. D., et al., 1988, "Tat protein from human immunodeficiency virus forms a metal-linked dimer", Science 240(4848):70-3 (abstract provided).*
Kuken, C., et al., 2001, HIV Sequence Compendium 2001, Theoretical Biology and Biophysics Group, Los Alamos National Laboratory.*

Novitsky et al. (2002) *J. Virol.* 76:10155-10168.
Rodman et al. (1993) *Proc. Natl. Acad. Sci. USA* 90:7719-7723.
Cafaro et al. (1999) *Nat. Med.* 5:643-650.
Re et al. (2001) *New Microbiol.* 24:197-205.
Gruters et al. (2002) *Vaccine* 20:2011-2015.
Allen et al. (2000) *Nature* 407:386-390.
Addo et al. (2001) *Proc. Natl. Acad. Sci. USA* 98:1781-1786.
Fanales-Belasio et al. (2002) *DNA Cell Biol.* 21:599-610.
Wu and Marsh (2001) *Science* 293:1503-1506.
Dorr et al. (2002) *EMBO J.* 21:2715-2723.
Nakatani (2002) *Structure* 10:443-444.
Mujtaba et al. (2002) *Mol. Cell* 9:575-586.
Deng, L., et al. "Accetylation of HIV-1 Tat by CBP/P300 Increases transcription of Integrated HIV-1 genome and enhances binding to core histones" Virol. 2000, 277:278-295.
Col, E. et al. The histone acetyltransferase, hGCN5, Interacts with and acetylates the HIV transctivator, Tat. Jul. 27, 2001, vol. 276, No. 30, pp. 28179-28184.
Bres, V., et al., Tat acetyl-acceptor lysines are important for human immunodeficiency virus type-1 replication. J. Biol. Chem. Jun. 21, 2002, vol. 277, No. 25, pp. 22215-22221.
Chirmule et al. Human Immunodeficiency Virus Tat Induces Functional Unresponsiveness in T Cells. Journal of Virology, 1995, vol. 69, No. 1, p. 492-498.
Lamhamedi-Cherradi et al. Qualitative and Quantitative Analysis of Human Cytotoxic T-lymphocyte Resonses to HIV-1 Proteins. AIDS 1992, 6:1249-1258.
Tähtinen et al. DNA Vaccination in Mice Using HIV-1 nef, rev and tat genes in self-replication pBN-vector. Vaccine 19 (2001) 2039-2047.
Bennasser and Bahraoui. HIV-1 Tat Protein Induces Interleukin-10 in Human Peripheral Blood Monocytes: Involvement of Protein Kinase C-βII and —FASEB J. 2002, 16, 546-554.
Agwale et al. A Tat subunit vaccine confers protective immunity against the immune-modulating activity of the human immunodeficiency virus type-1 Tat protein in mice. PNAS. 2002, vol. 99, No. 15, pp. 10037-10041.
Brake et al. Characterization of murine monoclonal antibodies to the tat protein from human immunodeficiency virus type 1. Journal of Virology. 1990, vol. 64, No. 2, pp. 962-965.

(Continued)

*Primary Examiner*—Jeffrey S. Parkin
(74) *Attorney, Agent, or Firm*—Paul A. Borden; Bozicevic, Field & Francis LLP

(57) ABSTRACT

The present invention provides compositions, including immunogenic compositions, comprising acetylated Tat protein of an immunodeficiency virus. The present invention further provides antibodies that specifically bind an acetylated Tat polypeptide. The present invention further provides methods of inducing an immune response to an immunodeficiency virus Tat protein in an individual. The present invention further provides methods of inhibiting transcriptional activation of an immunodeficiency virus in a cell of an individual.

26 Claims, 8 Drawing Sheets

OTHER PUBLICATIONS

Cohen et al. Pronounced acute immunosuppression in vivo mediated by HIV Tat challenge. PNAS. 1999, vol. 96, pp. 10842-10847.

Gallo, R. Tat as one key to HIV-induced immune pathogenesis and Pat toxoid as an important component of a vaccine. PNAS. 1999, vol. 96, pp. 8324-8326.

Gutheil et al. Human immunodeficiency virus 1 Tat binds to dipeptidyl aminopeptidase IV (CD26): A possible mechanism for Tat's immunosuppressive activity. PNAS. 1994, vol. 91, pp. 6594-6598.

Zocchi et al. HIV-1 Tat inhibits human natural killer cell function by blocking L-type calcium channels. The Journal of Immunology. 1998, vol. 161, pp. 2938-2943.

Cui et al., "Strong T cell type-1 immune responses to HIV-1 Tat (1-72) protein-coated nanoparticles" Vaccine 22 (2004) 2631-2640.

* cited by examiner

Tat alignment

FIG. 5B

```
         60              70              80   83 84        90              103
KRRQRRRPPQGSQTHQVSLSKQPTSQSRG-DPT GPKESKKKVERETETDPFD- (SEQ ID NO: 42)
KRRQRRRPPQGSQTHQVSLSKQPTSQSRG-DPT GPKE-------------- (SEQ ID NO: 43)
KRRQRRRAPQGSQTHQVSLSKQPTSQSRG-DPT GPKE-------------- (SEQ ID NO: 44)
KRRQRRRPPQGSQTHQVSLSKQPTSQPRG-DPT GPKE-------------- (SEQ ID NO: 45)
KRRQRRRPPQGSQTHQVSLSKQPTSQPRG-DPT GPKE-------------- (SEQ ID NO: 46)
KRRQRRRGPPQGSQTHQVSLSKQPTSQPRG-DPT GPKESKEKVERETETDPAVQ (SEQ ID NO: 47)
KRRQRRRAHQNSQTHQASLSKQPTSQPRG-DPT GPKE-------------- (SEQ ID NO: 48)
KRRQRRRAHQDSQNHQASLSKQPSSQTRG-DPT GPKEPKKEVEREAETDPLD- (SEQ ID NO: 49)
KRRQRRRAPDSSQNHQDSLSKQPSSQPRG-DPT GPKESKKEVERETETDPLD- (SEQ ID NO: 50)
KRRQRRRPSQGGQTHQDPIPKQPSSQPRG-NPT GPKE-------------- (SEQ ID NO: 51)
KRRQRRRPSQGGQTHQDPIPKQPSSQPRG-DPT GPKE-------------- (SEQ ID NO: 52)
KRRQRRRGPPQGGQAHQVPIPKQPSSQPRG-DPT GPKESKEKVESEAETDP--- (SEQ ID NO: 53)
KRRQRRKPPQGDQAHQVPIPEQPSSQSRG-DPT GPKK-------------- (SEQ ID NO: 54)
KRRQRRRPPQGNQAHQDPLPEQPSSQHRGDHPT GPKE-------------- (SEQ ID NO: 55)
KRKPRRGPPQGSKDHQTLIPKQPLPQSQR-VSA GQEESKKKVESKAKTDRFA- (SEQ ID NO: 56)
KRRQRRRAPQDSQTHQASLSKQPASQSRG-DPT GPTESKKKVERETETDPFD- (SEQ ID NO: 57)
KRRQRRRPPQDSQTHQSSLSKQPTSQLRG-DPT GPTESKKKVERETETDPVH- (SEQ ID NO: 58)
KRRQRRRAPQDSKTHQVSLSKQPASQPRG-DPT GPKESKKKVERETETDPED- (SEQ ID NO: 59)
KRRQRRRQRRA------------------- --- ------------------ (SEQ ID NO: 60)
KRRQRRRAPEDSQTHQVSLPKQPAPQFRG-DPT GPKESKKKVERETETHPVD- (SEQ ID NO: 61)
KRRQRRRAPQDSQTHQVSLPKQPASQARG-DPT GPKESKKKVERETETDPVD- (SEQ ID NO: 62)
KRRQRRRAPPDSEVHQVSLPKQPASQPQG-DPT GPKESKKKVERETETDPVH- (SEQ ID NO: 63)
KRRQRRRPPQDSQTHQVSLPKQPSSQQRG-DPT GPKESKKKVERETETDPDN- (SEQ ID NO: 64)
KRRQRRRPPQGSQTHQVSLSKQPTSQSRG-DPT GPKESKKKVERETETDPFD- (SEQ ID NO: 65)
```

IMMUNOGENIC COMPOSITIONS COMPRISING HIV-1 ACETYLATED TAT POLYPEPTIDES

CROSS-REFERENCE

This application claims the benefit of U.S. Provisional Patent Application No. 60/456,468, filed Mar. 19, 2003, which application is incorporated herein by reference in its entirety.

STATEMENT REGARDING FEDERALLY SPONSORED RESEARCH

The U.S. government may have certain rights in this invention, pursuant to grant no. AI40847 awarded by the National Institutes of Health.

FIELD OF THE INVENTION

The present invention is in the field of human immunodeficiency virus, and immunogenic compositions.

BACKGROUND OF THE INVENTION

Transcriptional activity of the integrated human immunodeficiency virus-1 (HIV-1) provirus is regulated by the concerted action of cellular transcription factors and the viral transactivator Tat. In the absence of Tat, HIV transcription is highly inefficient because the assembled RNA polymerase II complex cannot elongate efficiently on the viral DNA template. Tat is a unique viral transactivator that binds to an RNA stem-loop structure called TAR, which forms at the 5' extremity of all viral transcripts. Tat binds to TAR via its C-terminal arginine-rich motif (amino acids 49-57) that is essential for RNA binding and nuclear localization. The N-terminal transactivation domain of Tat (amino acids 1-48) interacts directly with CyclinT1, a component of the positive-acting transcription elongation factor (P-TEFb) complex. CyclinT1 recruits the cyclin-dependent kinase 9 (CDK-9), the catalytic subunit of the separately identified "Tat-associated kinase" (TAK). TAK/CDK-9 hyperphosphorylates the C-terminal domain (CTD) of the large subunit of the RNA polymerase II (RNApolII), leading to increased elongation efficiency of the polymerase complex.

HIV infection is currently treated with combination therapy, including protease inhibitors and reverse transcriptase inhibitors. Such therapy prolongs life, but does not rid the body of the infection. Furthermore, drug-resistant variants arise in a significant proportion of individuals being treated. Although a number of vaccines for HIV are currently in clinical trials, none has thus far been proven to be effective in treating or preventing HIV.

Despite the availability of treatments for HIV infection, there is a need in the art for improved reagents and methods for treating this deadly disease. The present invention addresses this need.

Literature

Novitsky et al. (2002) *J. Virol.* 76:10155-10168; Rodman et al. (1993) *Proc. Natl. Acad. Sci. USA* 90:7719-7723; Cafaro et al. (1999) *Nat. Med.* 5:643-650; Gibellini et al. (2001) *New Microbiol.* 24:197-205; Gruters et al. (2002) *Vaccine* 20:2011-2015; Allen et al. (2000) *Nature* 407:386-390; Addo et al. (2001) *Proc. Natl. Acad. Sci. USA* 98:1781-1786; Fanales-Belasio et al. (2002) *DNA Cell Biol.* 21:599-610; Wu and Marsh (2001) *Science* 293:1503-1506; Dorr et al. (2002) *EMBO J.* 21:2715-2723; Nakatani (2002) *Structure* 10:443-444; Bres et al. (2002) *EMBO J.* 21:2715-2723; Mujtaba et al. (2002) *Mol. Cell.* 9:575-586; U.S. Pat. No. 6,447,778.

SUMMARY OF THE INVENTION

The present invention provides compositions, including immunogenic compositions, comprising acetylated Tat protein of an immunodeficiency virus. The present invention further provides antibodies that specifically bind an acetylated Tat polypeptide. The present invention further provides methods of inducing an immune response to an immunodeficiency virus Tat protein in an individual. The present invention further provides methods of inhibiting transcriptional activation of an immunodeficiency virus in a cell of an individual.

BRIEF DESCRIPTION OF THE DRAWINGS

FIGS. 5A and 5B provide the amino acid sequences of several HIV-1 Tat polypeptides (SEQ ID NOs:42-65).

DEFINITIONS

Figure 1A:
FIGS. 1A-F depict generation of monoclonal and polyclonal antibodies specific for AcTat.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like. $NH_2$ refers to the free amino group present at the amino terminus of a polypeptide. COOH refers to the free carboxyl group present at the carboxyl terminus of a polypeptide. In keeping with standard polypeptide nomenclature, *J. Biol. Chem.*, 243 (1969), 3552-59 is used.

A "substantially isolated" or "isolated" polypeptide or antibody is one that is substantially free of the materials with which it is associated in nature. By substantially free is meant at least 50%, at least 70%, at least 80%, or at least 90% free of the materials with which it is associated in nature. As used herein, an "isolated" polypeptide also refers to fusion polypeptides, which, by virtue of origin or manipulation: (1) are not associated with all or a portion of a polypeptide with which it is associated in nature, (2) are linked to a polypeptide other than that to which it is linked in nature, or (3) does not occur in nature. In many embodiments, an isolated polypeptide or an isolated antibody is at least about 70%, at least about 80%, at least about 90%, at least about 95%, or at least about 99%, or more, pure.

The term "binds specifically," in the context of antibody binding, refers to high avidity and/or high affinity binding of an antibody to a specific polypeptide i.e., epitope of an acetylated Tat polypeptide. Antibody binding to an epitope on a specific acetylated Tat polypeptide (also referred to herein as "an acetylated Tat epitope") is preferably stronger than binding of the same antibody to any other epitope, particularly those which may be present in molecules in association with, or in the same sample, as the specific polypeptide of interest, e.g., binds more strongly to a specific acetylated Tat epitope than to a different acetylated Tat epitope so that by adjusting binding conditions the antibody binds almost exclusively to the specific acetylated Tat epitope and not to any other acetylated Tat epitope, and not to any other acetylated Tat polypeptide which does not comprise the epitope.

Antibodies which bind specifically to a subject polypeptide may be capable of binding other polypeptides at a weak, yet detectable, level (e.g., 10% or less of the binding shown to the polypeptide of interest). Such weak binding, or background binding, is readily discernible from the specific antibody binding to a subject polypeptide, e.g. by use of appropriate controls. In general, antibodies of the invention which bind to a specific acetylated Tat polypeptide with a binding affinity of $10^{-7}$ mole/l or more, e.g., $10^{-8}$ mole/l or more are said to bind specifically to the specific acetylated Tat polypeptide. In general, an antibody with a binding affinity of $10^{-6}$ mole/liter or less is not useful in that it will not bind an antigen at a detectable level using conventional methodology currently used.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease. In the context of immunodeficiency virus infection, the term "treatment" encompasses prevention of establishment of a systemic infection following initial contact with the virus; and prophylactic treatment of an individual not yet infected with the virus.

The term "effective amount" or "therapeutically effective amount" means a dosage sufficient to provide for treatment for the disease state being treated or to otherwise provide the desired effect (e.g., induction of an effective immune response, reduction in serum viral load, etc.). The precise dosage will vary according to a variety of factors such as subject-dependent variables (e.g., age, immune system health, etc.), the disease (e.g., the particular immunodeficiency virus), and the treatment being effected. In the case of an immunodeficiency virus, an "effective amount" is that amount necessary to substantially improve the likelihood of treating the infection, in particular that amount which improves the likelihood of successfully preventing infection or eliminating infection when it has occurred.

The terms "individual," "host," "subject," and "patient," used interchangeably herein, refer to a mammal, including, but not limited to, murines, felines, simians, humans, mammalian farm animals, mammalian sport animals, and mammalian pets. The term includes mammals that are susceptible to infection by an immunodeficiency virus.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as $CD4^+$ T lymphocytes, glial cells, macrophages, tumor cells, peripheral blood mononuclear cells (PBMC), and the like. The term "biological sample" encompasses a clinical sample, and also includes cells in culture, cell supernatants, tissue samples, organs, bone marrow, and the like.

The term "immunodeficiency virus" as used herein, refers to human immunodeficiency virus-1 (HIV-1); human immunodeficiency virus-2 (HIV-2); any of a variety of HIV subtypes and quasispecies; simian immunodeficiency virus (SIV); and feline immunodeficiency virus (FIV).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an acetylated Tat polypeptide" includes a plurality of such polypeptides and reference to "the immunogenic composition" includes reference to one or more immunogenic compositions and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides isolated acetylated Tat polypeptides. The present invention further provides compositions, including immunogenic compositions comprising an acetylated Tat polypeptide. Such polypeptides and compositions, e.g., immunogenic compositions, are useful for eliciting an immune response to an immunodeficiency virus, e.g., a human immunodeficiency virus (HIV).

The present invention further provides antibodies, including isolated antibodies, to acetylated Tat polypeptides, as well as compositions comprising a subject antibody. When administered to an individual infected with HIV, antibodies to acetylated Tat polypeptides reduce entry of acetylated Tat polypeptide into a cell (e.g., an HIV-infected cell), and are thus useful in therapeutic methods to treat an HIV infection.

The invention further provides methods of inducing an immune response to an acetylated Tat protein in an individual, the method generally involving administering to the individual an acetylated Tat protein in an amount effective to induce an immune response to HIV acetylated Tat protein.

The present invention further provides methods of inhibiting transcriptional activation of HIV in an individual, the method generally involving administering to an individual in need thereof an acetylated HIV Tat protein, such that antibodies to the acetylated Tat protein are produced. Alternatively, an antibody to an acetylated HIV Tat protein is administered to the individual. The antibodies bind to acetylated Tat protein in the serum of the individual and reduce entry of the acetylated Tat protein into the cell.

The invention is based in part on the observation that HIV Tat protein, which is poorly immunogenic, becomes highly immunogenic when acetylated. Thus, acetylated Tat is useful in an immunogenic composition for inducing an immune response to HIV Tat protein. The present invention takes advantage of the fact that Tat protein is produced early in HIV infection. Thus, a reduction in the level and/or activity of Tat protein, e.g., acetylated Tat protein, blocks HIV production at an early stage of the HIV life cycle. The present invention further takes advantage of the fact that Tat does not exhibit as high a degree of amino acid variability among HIV isolates as do other HIV proteins. This relative conservation of amino acid sequence suggests that conservation of Tat amino acid sequence is important to HIV production. Thus, the present compositions and methods are advantageous in that the target virus is less likely to develop viable escape variants.

Isolated Acetylated Tat Polypeptides

The present invention provides isolated acetylated Tat polypeptides. A subject acetylated Tat polypeptide is isolated. In some embodiments, an acetylated Tat polypeptide is isolated from a naturally-occurring source of acetylated Tat polypeptide. In some embodiments, an acetylated Tat polypeptide is synthetic (e.g., produced by synthetic means in a laboratory, e.g., using standard peptide synthesis methods). In some embodiments, a subject acetylated Tat polypeptide is coupled to a carrier. The present invention further provides compositions comprising an acetylated Tat polypeptide, including immunogenic compositions.

A subject acetylated Tat polypeptide includes all or a portion of any known Tat protein from any immunodeficiency virus, provided that the polypeptide comprises at least one acetylated lysine residue, and includes at least three, four, five, or more additional amino acids on the amino-terminal side of the acetylated lysine residue and at least three, four, five, or more additional amino acids on the carboxyl-terminal side of the acetylated lysine residue. Acetylated lysine residues include, but are not limited to, K28, K41, and K50. In some embodiments, a subject acetylated Tat polypeptide includes one acetylated lysine residue. In other embodiments, a subject acetylated Tat polypeptide includes two acetylated lysine residues. In other embodiments, a subject acetylated Tat polypeptide includes three or more acetylated lysine residues.

In certain embodiments, a subject acetylated Tat polypeptide comprises amino acid sequences corresponding to HIV-1. In many embodiments, a subject acetylated Tat polypeptide comprises acetylated Lysine-50 (Ac-Lys50) and at least about three, four, five, or more additional amino acids on the amino-terminal side of amino acid 50 and three, four, five, or more additional amino acids on the carboxyl-terminal side of amino acid 50, where Lys50 is acetylated. In some embodiments, a subject acetylated Tat polypeptide is acetylated on amino acid 50 (Lys).

An acetylated Tat polypeptide is generally from about 7 to about 72 amino acids in length, e.g., from about 7 amino acids to about 10 amino acids, from about 10 amino acids to about 15 amino acids, from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 45 amino acids, from about 45 amino acids to about 50 amino acids, from about 50 amino acids to about 55 amino acids, from about 55 amino acids to about 60 amino acids, from about 60 amino acids to about 65 amino acids, or from about 65 amino acids to about 70 amino acids in length, up to the full-length Tat polypeptide.

In some embodiments, a subject acetylated Tat polypeptide includes heterologous amino acid sequences, e.g., a subject acetylated Tat polypeptide may be a fusion protein that comprises an acetylated Tat polypeptide and a fusion partner, where the fusion partner is a heterologous polypeptide (e.g., a polypeptide other than Tat). Heterologous polypeptides are polypeptides other than Tat, and include, but are not limited to, polypeptide carriers (discussed in more detail below); immunological tags such as epitope tags, including, but not limited to, hemagglutinin, FLAG, and the like; proteins that provide for a detectable signal, including, but not limited to, fluorescent proteins, enzymes (e.g., β-galactosidase, alkaline phosphatase, luciferase, horse radish peroxidase, etc.), and the like; polypeptides that facilitate purification or isolation of the fusion protein, e.g., metal ion binding polypeptides such as 6His tags (e.g., acetylated Tat/6His), glutathione-S-transferase; polypeptides that facilitate transport across a eukaryotic cell membrane; and the like.

Fluorescent proteins include, but are not limited to, a green fluorescent protein (GFP), including, but not limited to, a "humanized" version of a GFP, e.g., wherein codons of the naturally-occurring nucleotide sequence are changed to more closely match human codon bias; a GFP derived from *Aequoria victoria* or a derivative thereof, e.g., a "humanized" derivative such as Enhanced GFP, which are available commercially, e.g., from Clontech, Inc.; a GFP from another species such as *Renilla reniformis, Renilla mulleri,* or *Ptilosarcus guernyi*, as described in, e.g., WO 99/49019 and Peelle et al. (2001) *J. Protein Chem.* 20:507-519; "humanized" recombinant GFP (hrGFP) (Stratagene); any of a variety of fluorescent and colored proteins from Anthozoan species, as described in, e.g., Matz et al. (1999) *Nature Biotechnol.* 17:969-973; and the like. Where the fusion partner is an enzyme that yields a detectable product, the product can be detected using an appropriate means, e.g., β-galactosidase can, depending on the substrate, yield colored product, which is detected spectrophotometrically, or a fluorescent product; luciferase can yield a luminescent product detectable with a luminometer; etc.

In some embodiments, an acetylated Tat polypeptide is detectably labeled. Various labels include radioisotopes, fluorescers (e.g., fluorescent dyes), chemiluminescers, enzymes, a member of a specific binding pair, particles, e.g. magnetic particles, and the like. Specific binding pairs include, but are not limited to, biotin and streptavidin; digoxin and antidigoxin; lectin and carbohydrate moieties; antibody and hapten; antibody and antigen; etc.

Figure 5A:
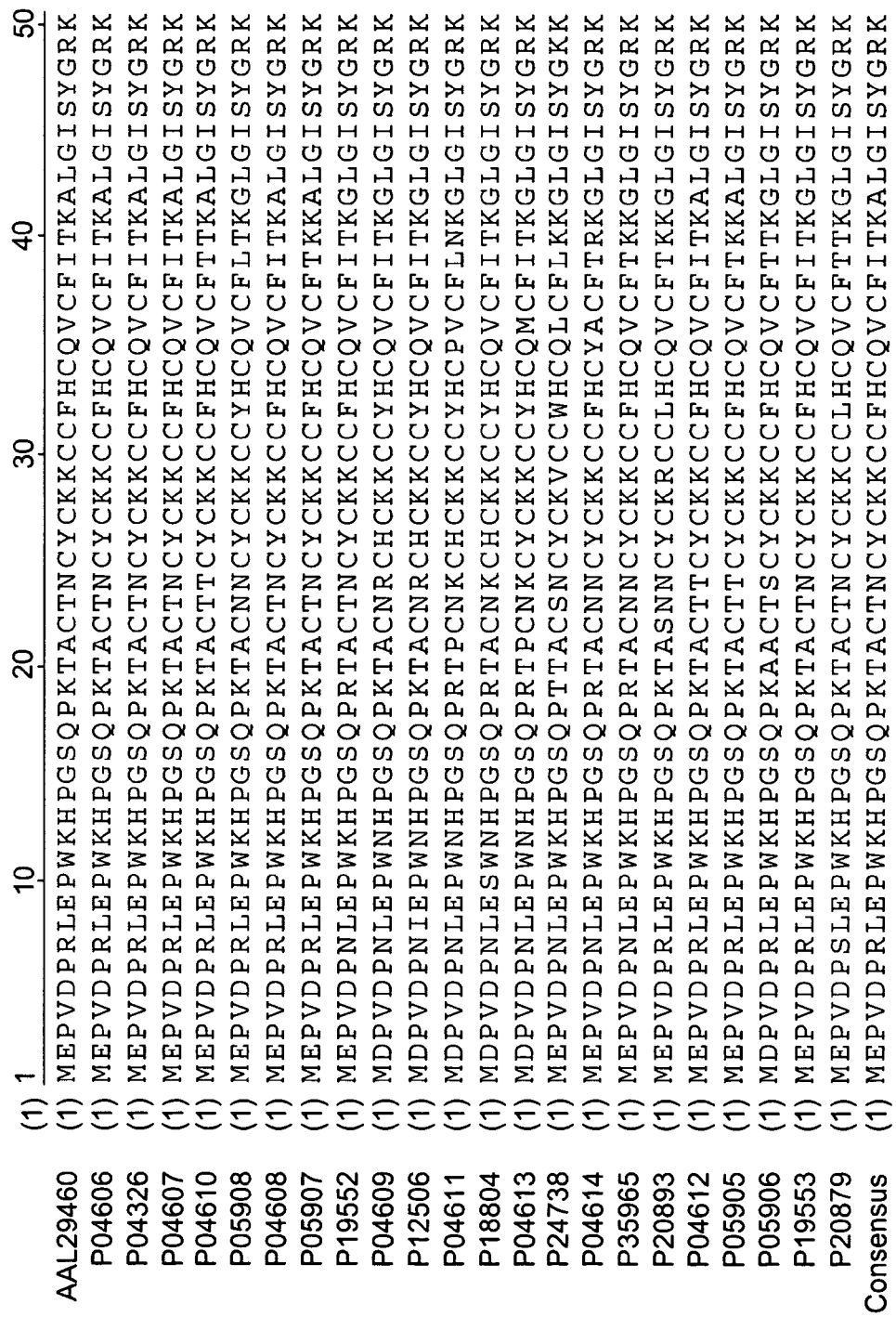

As noted above, a subject acetylated Tat polypeptide can be isolated from a naturally-occurring source of Tat polypeptide; or can be synthesized. The amino acid sequences of HIV Tat polypeptides are known, and any of these sequences can be included in a subject acetylated Tat polypeptide. Numerous HIV Tat protein amino acid sequences are found under GenBank, and any of these publicly available sequences can be used in the present invention. Exemplary, non-limiting, HIV Tat protein amino acid sequences are found under GenBank Accession Nos. AAO26250, AAO26252, AAO26254, AAO26258, AAO26260, AAO26262, AAO26264, AAO26266, AAO26268, AAO26270, AAO26272, AAO26274, AAO26276, AAO26278, AAO26280, AAO26282, AAO26284, AAO26286, AAO26288, AAO26290, AAO26292, AAO26294, AAO26296, AAO26298, AAO26300, AAO26302, AAO26304, AAO26306, AAO26308; AAB50256; AAL12204; AAL12195; AAL12186; AAL12177; AAN47131; AAN47122; AAN47113; AAN47104; AAN03332; AAN03323; AAN03314; AAN03305; AAN03296; AAN03287; AAN03278; AAN31592; AAN64126; AAN64117; AAN64108; AAN64099; AAN64090; AAN64080; K02013; AAL29460; and as shown in FIGS. 5A and 5B. Additional HIV Tat amino acid sequences are found in Peloponese et al. (1999) *J. Biol. Chem.* 274:11473-11478; and Goldstein (1996) *Nat. Med.* 2:960-964.

In some embodiments, an acetylated Tat polypeptide comprises from about 7 to about 100 amino acids in length, e.g., from about 7 amino acids to about 10 amino acids, from about 10 amino acids to about 15 amino acids, from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 45 amino acids, from about 45 amino acids to about 50 amino acids, from about 50 amino acids to about 55 amino acids, from about 55 amino acids to about 60 amino acids, from about 60 amino acids to about 65 amino acids, from about 65 amino acids to about 70 amino acids, from about 70 amino acids to about 75 amino acids, from about 75 amino acids to about 80 amino acids, from about 80 amino acids to about 90 amino acids, or from about 90 amino acids to about 100 amino acids in length, up to the full-length Tat polypeptide, of any one of the amino acid sequence set forth in FIGS. 5A and 5B.

In some embodiments, a subject acetylated Tat polypeptide comprises the following consensus sequence (where amino acid sequences are provided from amino-terminus (N-terminus) to carboxyl-terminus (C-terminus): Lys-(Ala or Gly)-Leu-Gly-Ile-Ser-Tyr-Gly-Arg-<u>Lys</u>-Lys-Arg-(Arg or Lys)-(Gln or His)-Arg-Arg-(Arg or Gly or Lys or Ser)-(Pro or Ala or Thr)-(Gln or Pro or Thr) (SEQ ID NO:01), wherein one or more of the lysines is acetylated. In some embodiments, the lysine corresponding to Lys-50 in the full-length protein is acetylated (e.g., the underlined Lys in SEQ ID NO:01).

In a particular embodiment, a subject acetylated Tat polypeptide includes the amino acid sequence Ser-Tyr-Gly-Arg-AcLys-Lys-Lys-Arg-Arg-Gln-Arg (SEQ ID NO:02).

Exemplary, non-limiting acetylated Tat polypeptides include those shown below (where amino acid sequences are provided from amino-terminus (N-terminus) to carboxyl-terminus (C-terminus)):

Ser-Tyr-Gly-Arg-acetylated Lys-Lys-Arg-Arg-Gln-Arg-Cys (SEQ ID NO:03);

Ser-His-Gly-Arg-acetylated Lys-Lys-Arg-Arg-Gln-Arg-Cys (SEQ ID NO:04);

Lys-Gly-Leu-Gly-Ile-Ser-Tyr-Gly-Arg-acetylated Lys-Lys-Arg-Arg-Gln-Arg-Arg-Arg-Thr-Pro-Gln (SEQ ID NO:05);

Lys-Ala-Leu-Gly-Ile-Ser-Tyr-Gly-Arg-acetylated Lys-Lys-Arg-Arg-Gln-Arg-Arg-Arg-Thr-Ser-Gln (SEQ ID NO:06);

Lys-Ala-Leu-Gly-Ile-Ser-Tyr-Gly-Arg-acetylated Lys-Lys-Arg-Arg-Gln-Arg-Arg-Arg-Thr-Ala-Gln (SEQ ID NO:07);

Lys-Gly-Leu-Gly-Ile-Ser-His-Gly-Arg-acetylated Lys-Lys-Arg-Arg-Gln-Arg-Arg-Arg-Thr-Pro-Pro (SEQ ID NO:08);

Lys-Gly-Leu-Gly-Ile-Ser-Tyr-Gly-Arg-acetylated Lys-Lys-Arg-Arg-Gln-Arg-Arg-Arg-Ala-Ala-Gln (SEQ ID NO:09);

Lys-Gly-Leu-Gly-Ile-Ser-Tyr-Gly-Arg-acetylated Lys-Lys-Arg-Arg-Gln-Arg-Arg-Arg-Ala-Pro-Gln (SEQ ID NO:10);

Lys-Gly-Leu-Gly-Ile-Ser-Tyr-Gly-Arg-acetylated Lys-Lys-Arg-Arg-Gln-Arg-Arg-Arg-Ser-Pro-Gln (SEQ ID NO:11);

Lys-Gly-Leu-Gly-Ile-Ser-Tyr-Gly-Arg-acetylated Lys-Lys-Arg-Arg-Gln-Arg-Arg-Arg-Pro-Pro-Gln (SEQ ID NO:12);

Lys-Gly-Leu-Gly-Ile-Ser-Tyr-Gly-Arg-acetylated Lys-Lys-Arg-Arg-Gln-Arg-Arg-Arg-Thr-His-Gln (SEQ ID NO:13);

Gly-Leu-Gly-Ile-Ser-Tyr-Gly-Arg-acetylated Lys-Lys-Arg-Arg-Gln-Arg-Arg-Arg-Thr-Pro-(SEQ ID NO:14);

Ala-Leu-Gly-Ile-Ser-Tyr-Gly-Arg-acetylated Lys-Lys-Arg-Arg-Gln-Arg-Arg-Arg-Thr-Ser (SEQ ID NO:15);

Ala-Leu-Gly-Ile-Ser-Tyr-Gly-Arg-acetylated Lys-Lys-Arg-Arg-Gln-Arg-Arg-Arg-Thr-Ala (SEQ ID NO:16);

Gly-Leu-Gly-Ile-Ser-His-Gly-Arg-acetylated Lys-Lys-Arg-Arg-Gln-Arg-Arg-Arg-Thr-Pro (SEQ ID NO:17);

Gly-Leu-Gly-Ile-Ser-Tyr-Gly-Arg-acetylated Lys-Lys-Arg-Arg-Gln-Arg-Arg-Arg-Ala-Ala (SEQ ID NO:18);

Gly-Leu-Gly-Ile-Ser-Tyr-Gly-Arg-acetylated Lys-Lys-Arg-Arg-Gln-Arg-Arg-Arg-Ala-Pro (SEQ ID NO:19);

Gly-Leu-Gly-Ile-Ser-Tyr-Gly-Arg-acetylated Lys-Lys-Arg-Arg-Gln-Arg-Arg-Arg-Ser-Pro (SEQ ID NO:20);

Gly-Leu-Gly-Ile-Ser-Tyr-Gly-Arg-acetylated Lys-Lys-Arg-Arg-Gln-Arg-Arg-Arg-Pro-Pro (SEQ ID NO:21);

Gly-Leu-Gly-Ile-Ser-Tyr-Gly-Arg-acetylated Lys-Lys-Arg-Arg-Gln-Arg-Arg-Arg-Thr-His (SEQ ID NO:22);

Lys-Gly-Leu-Gly-Ile-Ser-Tyr-Gly-Arg-acetylated Lys-Lys-Arg-Arg-His-Arg-Arg-Arg-Thr-Pro-Gln (SEQ ID NO:23).

In some embodiments, a subject acetylated Tat polypeptide includes one or more additional amino acids not found in a naturally-occurring Tat polypeptide. Such amino acids include amino acids added to the amino-terminus and/or the carboxyl-terminus of an acetylated Tat polypeptide. Amino acids added to an acetylated Tat polypeptide include amino acids that serve as linkers, e.g., to a carrier polypeptide or other polypeptide, as discussed above. Linking can be performed to any amino acid that contains an active group, including, but not limited to, amino acids with a free $NH_2$ group, e.g., lysine, arginine, asparagine, and glutamine; a free NH$_2$ group of an amino terminal amino acid; amino acids with sulfhydryl groups, e.g., cysteine, or an amino acid to which an SH$_2$ group has been chemically added; amino acids with carboxyl groups, e.g., aspartic acid, glutamic acid; and a COOH group of a carboxyl-terminal amino acid.

In some embodiments, a subject acetylated Tat polypeptide includes an additional cysteine residue appended to the C-terminus. A cysteine residue serves as a linkage site for linking to a carrier. For example, a subject acetylated Tat polypeptide includes any one of SEQ ID NOs:1, 2, and 5-23 with an additional cysteine on the C-terminus.

In some specific embodiments, a subject acetylated Tat polypeptide comprises the sequence Ser-Tyr-Gly-Arg-acetylated Lys-Lys-Arg-Arg-Gln-Arg-Cys (SEQ ID NO:03).

Multimers

In some embodiments, an acetylated Tat polypeptide is multimerized, e.g., two or more acetylated Tat polypeptides are linked in tandem. Multimers include dimers, trimers, tetramers, pentamers, etc. Monomeric acetylated Tat polypeptides are linked to one another directly or via a linker. Thus, in some embodiments, a subject acetylated Tat polypeptide has the formula X—(Y)$_{0-40}$—X, where X is an acetylated Tat polypeptide, and Y is a linker. Where a linker is used, Y is one or more amino acids, or other linking groups.

Where Y is a spacer peptide, it is generally of a flexible nature, although other chemical linkages are not excluded. Currently, it is contemplated that the most useful linker sequences will generally be peptides of between about 2 and about 40 amino acids in length, e.g., from about 2 amino acids to about 10 amino acids, from about 10 amino acids to about 20 amino acids, or from about 6 amino acids to about 25 amino acids in length. These linkers are generally produced by using synthetic, linker-encoding oligonucleotides to couple the proteins. Peptide linkers with a degree of flexibility will generally be used. The linking peptides may have virtually any amino acid sequence, bearing in mind that the preferred linkers will have a sequence that results in a generally flexible peptide. The use of small amino acids, such as glycine and alanine, are of use in creating a flexible peptide. Exemplary peptide linkers include (Gly)$_{2-40}$, (Ser)$_{2-40}$, and (Ala)$_{2-40}$. The creation of such sequences is routine to those of skill in the art. A variety of different linkers are commercially available and are considered suitable for use according to the present invention.

Amino acid sequences rich in alanine and proline residues are known to impart flexibility to multi-domain protein structures. For example, such sequences link the domains of the so-called E2 components of the 2-oxo acid dehydrogenase complexes, such as pyruvate dehydrogenase complex and 2-oxo glutarate dehydrogenase complex. Alanine-proline rich regions are also found in myosin light chains. Exemplary linkers for use in the invention have a combination of glycine, alanine, proline and methionine residues, such as AAAGGM (SEQ ID NO:24); AAAGGMPPAAAGGM (SEQ ID NO:25); AAAGGM (SEQ ID NO:26); and PPAAAGGM$_2$ (SEQ ID NO:27). However, any flexible linker generally between about 2 amino acids and about 40 amino acids, e.g., from about 6 amino acids to about 10 amino acids in length may be used. Linkers may have virtually any sequence that results in a generally flexible peptide, including alanine-proline rich sequences of the type exemplified above.

Linkages for homo- or hetero-polymers or for coupling to carriers can be provided in a variety of ways. For example, cysteine residues can be added at both the amino- and carboxy-termini, where the peptides are covalently bonded via controlled oxidation of the cysteine residues. Also useful are a large number of heterobifunctional agents which generate a disulfide link at one functional group end and a peptide link at the other, including N-succidimidyl-3-(2-pyridyldithio) proprionate (SPDP). This reagent creates a disulfide linkage between itself and a cysteine residue in one protein and an amide linkage through the amino on a lysine or other free amino group in the other. A variety of such disulfide/amide forming agents are known. See, for example, Immun. Rev. 62:185 (1982). Other bifunctional coupling agents form a thioether rather than a disulfide linkage. Many of these thio-ether forming agents are commercially available and include reactive esters of 6-maleimidocaproic acid, 2 bromoacetic acid, 2-iodoacetic acid, 4-(N-maleimido-methyl)cyclohexane-1-carboxylic acid and the like. The carboxyl groups can be activated by combining them with succinimide or 1-hydroxy-2-nitro-4-sulfonic acid, sodium salt. A particularly preferred coupling agent is succinimidyl 4-(N-maleimidomethyl)cyclohexane-1-carboxylate (SMCC). Of course, it will be understood that linkage should not substantially interfere with either of the linked groups to function as an immunogen.

Carriers

In some embodiments, and acetylated Tat polypeptide is linked to a carrier. The term "linked," as used herein interchangeably with the term "coupled," refers to proximately associated, e.g., the acetylated Tat polypeptide and the carrier are in close spatial proximity. In some embodiments, the linkage is a covalent linkage. In other embodiments, the linkage is a non-covalent linkage. In some embodiments, the acetylated Tat polypeptide is linked directly to the carrier. In other embodiments, the acetylated Tat polypeptide is linked indirectly, e.g., via a linker molecule. Examples of suitable carriers include large, slowly metabolized macromolecules such as: proteins; polysaccharides, such as sepharose, agarose, cellulose, cellulose beads and the like; polymeric amino acids such as polyglutamic acid, polylysine, and the like; amino acid copolymers; inactivated virus particles; inactivated bacterial toxins such as toxoid from diphtheria, tetanus, cholera, leukotoxin molecules; liposomes; inactivated bacteria; dendritic cells; and the like. Carriers are described in further detail below.

Suitable carriers are well known in the art, and include, e.g., thyroglobulin, albumins such as human serum albumin, tetanus toxoid; Diphtheria toxoid; polyamino acids such as poly(D-lysine:D-glutamic acid); VP6 polypeptides of rotaviruses; influenza virus hemagglutinin, influenza virus nucleoprotein; hepatitis B virus core protein, hepatitis B virus surface antigen; purified protein derivative (PPD) of tuberculin from *Mycobacterium tuberculosis*; inactivated *Pseudomonas aeruginosa* exotoxin A (toxin A); Keyhole Limpet Hemocyanin (KLH); filamentous hemagglutinin (FHA) of *Bordetella pertussis*; T helper cell (Th) epitopes of tetanus toxoid (TT) and *Bacillus* Calmette-Guerin (BCG) cell wall; recombinant 10 kDa, 19 kDa and 30-32 kDa proteins from *M. leprae* or from *M. tuberculosis*, or any combination of these proteins; and the like. See, e.g., U.S. Pat. No. 6,447,778 for a discussion of carriers methods of conjugating-peptides to carriers.

*Pseudomonas aeruginosa* exotoxin A (toxin A) has been used effectively as a carrier in conjugate vaccines. *Pseudomonas aeruginosa* exotoxin A may be purified from the supernatant of fermentor-grown cultures of *Pseudomonas aeruginosa* PA 103. Toxin A has been classified as a superantigen based upon results in animals. Toxin A can be completely and irreversibly detoxified by covalent coupling to adipic acid dihydrazide (ADH), a 4 carbon spacer molecule. This step destroys the ADPR-transferase activity of the toxin molecule, hence rendering it nontoxic. The non-reacted hydrazide group can be used to covalently couple a polypeptide to toxin A. Toxin A may also be coupled to a polypeptide using a carbodiimide reagent.

PPD-peptide conjugates are conveniently prepared with glutaraldehyde as coupling agent. See, e.g., Rubinstein et al. (1995) *AIDS* 9:243-51.

The methods by which a subject polypeptide is conjugated with a carrier include disulfide linkages through a C terminal peptide cysteine linkage, coupling with glutaraldehyde solution for two hours, coupling with tyrosine, or coupling with water soluble carbodiimide.

In some embodiments, a subject acetylated Tat polypeptide is lipidated. Lipidation increases a cytotoxic T cell (CTL) response to the peptide that is linked to the lipid. The lipid residue, such as palmitic acid or the like, is attached to the amino terminus of the peptide. The lipid can be attached directly to the peptide, or, indirectly via a linkage, such as a Ser-Ser, Gly, Gly-Gly, Ser linkage or the like. As another example, *E. coli* lipoprotein, such as tripalmitoyl-S-glyceryl-cysteinyl-seryl-serine ($P_3$ CSS), can be used to prime specific CTL when covalently attached to the peptide. See, Deres et al., *Nature* 342:561-564 (1989). An acetylated Tat polypeptide can be conjugated with uncharged fatty acid residues of different chain lengths and degrees of unsaturation, ranging from acetic to stearic acid as well as to negatively charged succinyl residues via the appropriate carboxylic acid anhydrides. See, e.g., U.S. Pat. No. 6,419,931.

An acetylated Tat polypeptide may be conjugated directly or indirectly, e.g., via a linker molecule, to a carrier. A wide variety of linker molecules are known in the art and can be used in the conjugates. The linkage from the peptide to the carrier may be through a peptide reactive side chain, or the N- or C-terminus of the peptide. A linker may be an organic, inorganic, or semi-organic molecule, and may be a polymer of an organic molecule, an inorganic molecule, or a co-polymer comprising both inorganic and organic molecules.

If present, the linker molecules are generally of sufficient length to permit the acetylated Tat polypeptide and a linked carrier to allow some flexible movement between the acetylated Tat polypeptide and the carrier. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to polypeptides may be used in light of this disclosure.

Preparation of Acetylated Tat Polypeptide

A subject acetylated Tat polypeptide may be synthesized chemically or enzymatically, may be produced recombinantly, may be isolated from a natural source, or a combination of the foregoing. A subject polypeptide may be isolated from natural sources using standard methods of protein purification known in the art, including, but not limited to, HPLC, exclusion chromatography, gel electrophoresis, affinity chromatography, or other purification technique. One may employ solid phase peptide synthesis techniques, where such techniques are known to those of skill in the art. See Jones, *The Chemical Synthesis of Peptides* (Clarendon Press, Oxford) (1994). Generally, in such methods a peptide is produced through the sequential additional of activated monomeric units to a solid phase bound growing peptide chain. Peptides can be synthesized in solution or on a solid support in accordance with conventional techniques. Various automatic synthesizers are commercially available and can be used in accordance with known protocols. See, for example, Stewart and Young, Solid Phase Peptide Synthesis, 2d. ed., Pierce Chemical Co. (1984); Tam et al., J. Am. Chem. Soc. 105:6442 (1983); Merrifield, Science 232:341-347 (1986); and Barany and Merrifield, The Peptides, Gross and Meienhofer, eds., Academic Press, New York, pp. 1-284 (1979), each of which is incorporated herein by reference. Well-established recombinant DNA techniques can be employed for production of a subject polypeptide.

For production of a subject acetylated Tat polypeptide by recombinant means, the polynucleotide comprising a nucleotide sequence encoding Tat ("a Tat polynucleotide") is expressed in any convenient expression system, including, for example, bacterial, yeast, insect, amphibian and mammalian systems. Suitable vectors and host cells are described in U.S. Pat. No. 5,654,173. In the expression vector, a Tat polynucleotide is linked to a regulatory sequence as appropriate to obtain the desired expression properties. These regulatory sequences can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the subject species from which the subject nucleic acid is obtained, or may be derived from exogenous sources.

Expression vectors generally have convenient restriction sites located near the promoter sequence to provide for the insertion of nucleic acid sequences encoding heterologous proteins. A selectable marker operative in the expression host may be present.

Expression cassettes may be prepared comprising a transcription initiation region, the gene or fragment thereof, and a transcriptional termination region. After introduction of the expression cassette containing a Tat polynucleotide, the cells containing the construct may be selected by means of a selectable marker, the cells expanded and then used for expression.

The above described expression systems may be employed with prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, e.g. COS 7 cells, HEK 293, CHO, Xenopus Oocytes, etc., may be used as the expression host cells. In some situations, it is desirable to express the gene in eukaryotic cells, where the expressed protein will benefit from native folding and post-translational modifications. Small peptides can also be synthesized in the laboratory. Polypeptides that are subsets of the complete protein sequence may be used to identify and investigate parts of the protein important for function. Specific expression systems of interest include bacterial, yeast, insect cell and mammalian cell derived expression systems, which expression systems are well known in the art.

Acetylation

In some embodiments, a subject Tat polypeptide is acetylated in vitro, either after synthesis or during synthesis, or, e.g., after isolation from a naturally-occurring source of a Tat polypeptide. For example, where a subject Tat polypeptide is prepared synthetically in vitro, a Tat polypeptide is acetylated in a solution comprising 50 mM HEPES, pH 8, 10% glycerol, 1 mM DTT, 10 mM sodium butyrate, and 20 nmol acetyl-coenzyme A (AcCoA) in the presence of an acetyl transferase for 2 hours at 30° C. See, e.g., Ott et al. (1999) *Curr. Biol.* 9:1489-1492. An acetylated Tat protein can be generated as described in, e.g., Dorr et al. (2002) *EMBO J* 21:2715-2723; or Peloponese (1999) *J. Biol. Chem.* 274:11473-11478.

In other embodiments, a Tat polypeptide is acetylated by a living cell, e.g., the acetylated lysine is incorporated during synthesis of the Tat polypeptide. Tat acetylation in a eukaryotic cell is mediated by intracellular acetyltransferases, e.g., histone acetyl transferase (HAT), which catalyzes the transfer of an acetyl group from AcCoA to the epsilon amino group of lysine. Exemplary HATs include GCN5, MYST, p300/CBP, and nuclear receptors. Acetylated Tat polypeptide synthesized by a living eukaryotic cell is recovered using standard methods for protein purification. In some embodiments, the Tat polypeptide that is acetylated by a living eukaryotic cell is a fusion protein comprising a moiety that facilitates purification (e.g., a binding moiety), e.g., GST, 6H is, etc., and the acetylated Tat polypeptide is purified using a separation medium appropriate to the binding moiety.

Compositions

The present invention provides compositions comprising a subject acetylated Tat polypeptide, which in some embodiments are immunogenic compositions. Compositions comprising a subject acetylated Tat polypeptide may include a buffer, which is selected according to the desired use of the acetylated Tat polypeptide, and may also include other substances appropriate to the intended use. Those skilled in the art can readily select an appropriate buffer, a wide variety of which are known in the art, suitable for an intended use. In some instances, the composition can comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", 19$^{th}$ Ed. (1995), or latest edition, Mack Publishing Co; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

Pharmaceutical compositions can be prepared in various forms, such as granules, tablets, pills, suppositories, capsules, suspensions, sprays, suppositories, transdermal applications (e.g., patches, etc.), salves, lotions and the like. Pharmaceutical grade organic or inorganic carriers and/or diluents suitable for oral and topical use can be used to make up compositions containing the therapeutically active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

When used as an immunogenic composition, a subject acetylated Tat polypeptide can be formulated in a variety of ways. In general, a subject immunogenic composition is formulated according to methods well known in the art using suitable pharmaceutical carrier(s) and/or vehicle(s). A suitable vehicle is sterile saline. Other aqueous and non-aqueous isotonic sterile injection solutions and aqueous and non-aqueous sterile suspensions known to be pharmaceutically acceptable carriers and well known to those of skill in the art may be employed for this purpose.

Optionally, an immunogenic composition of the invention may be formulated to contain other components, including, e.g., adjuvants, stabilizers, pH adjusters, preservatives and the like. Such components are well known to those of skill in the vaccine art. Adjuvants include, but are not limited to, aluminum salt adjuvants (Nicklas (1992) *Res. Immunol.* 143:489-493); saponin adjuvants; Ribi's adjuvants (Ribi ImmunoChem Research Inc., Hamilton, Mont.); Montanide ISA adjuvants (Seppic, Paris, France); Hunter's TiterMax adjuvants (CytRx Corp., Norcross, Ga.); Gerbu adjuvants (Gerbu Biotechnik GmbH, Gaiberg, Germany); ISCOM® adjuvants (CSL Ltd.); and nitrocellulose (Nilsson and Larsson (1992) *Res. Immunol.* 143:553-557). In addition, other components that may modulate an immune response may be included in the formulation, including, but not limited to, cytokines, such as interleukins; colony-stimulating factors (e.g., GM-CSF, G-CSF, and the like); and tumor necrosis factor.

Therapeutic agents that can be formulated together with one or more additional therapeutic agents. Suitable additional therapeutic agents include, but are not limited to, anti-inflammatory, anti-viral, anti-fungal, anti-mycobacterial, antibiotic, amoebicidal, trichomonocidal, analgesic, anti-neoplastic, anti-hypertensives, anti-microbial and/or steroid drugs, to treat antiviral infections. In some embodiments, a combination of one or more acetylated Tat polypeptides is formulated with one or more of the following; beta-lactam antibiotics, tetracyclines, chloramphenicol, neomycin, gramicidin, bacitracin, sulfonamides, nitrofurazone, nalidixic acid, cortisone, hydrocortisone, betamethasone, dexamethasone, fluocortolone, prednisolone, triamcinolone, indomethacin, sulindac, acyclovir, amantadine, rimantadine, recombinant soluble CD4 (rsCD4), a fusion inhibitor (e.g., a T20 peptide, a T-1249 peptide; Trimeris); an anti-CD4 antibody (e.g., an anti-CD4 antibody from Tanox, Inc.); an anti-CCR5 antibody (e.g., Pro 140); a CXCR4 blocker (e.g., AMD 3100); an HIV entry inhibitor (e.g., Pro-542; Progenics); a CCR5 blocker (e.g., SCH-C, SCH-D; Schering Plough); anti-receptor antibodies (e.g., for rhinoviruses), nevirapine (Viramune®), emiravine (Coactinon®), cidofovir (Vistide™), trisodium phosphonoformate (Foscarnet™), famcyclovir, pencyclovir, valacyclovir, nucleic acid/replication inhibitors, interferon, zidovudine (AZT, Retrovir™), didanosine (dideoxyinosine, ddI, Videx™), stavudine (d4T, Zerit™), zalcitabine (dideoxycytosine, ddC, Hivid™), nevirapine (Viramune™), lamivudine (Epivir™, 3TC), protease inhibitors, saquinavir (Invirase™, Fortovase™), ritonavir (Norvir™), nelfinavir (Viracept™), efavirenz (Sustiva™), abacavir (Ziagen™), amprenavir (Agenerase™) indinavir (Crixivan™), ganciclovir, AzDU, delavirdine (Rescriptor™), kaletra, trizivir, rifampin, clarithromycin, erythropoietin, colony stimulating factors (G-CSF and GM-CSF), non-nucleoside reverse transcriptase inhibitors, nucleoside reverse transcriptase inhibitors, HIV protease inhibitors, adriamycin, fluorouracil, methotrexate, asparaginase and combinations thereof.

In some embodiments, a subject composition comprising an acetylated Tat polypeptide comprises two or more acetylated Tat polypeptides, e.g., the composition is heterogeneous with respect to acetylated Tat polypeptides. For example, a subject composition comprises two or more of the polypeptides having amino acid sequences set forth in SEQ ID NO:1-23. Thus, in some embodiments, a subject composition comprises a first acetylated Tat polypeptide, and at least a second acetylated Tat polypeptide, wherein the first and the second acetylated Tat polypeptides differ in amino acid sequence by at least one amino acid.

In other embodiments, a subject composition comprises one or more acetylated Tat polypeptides and in addition, comprises a Tat polypeptide that is non-acetylated. A subject acetylated Tat polypeptide can be formulated together with one or more polypeptides comprising an amino acid sequence from about amino acid 1 to about amino acid 45, from about amino acid 5 to about amino acid 40, from about amino acid 10 to amino acid 35, from about amino acid 15 to about amino acid 30, from about amino acid 20 to about amino acid 25, from about amino acid 1 to about amino acid 10, from about amino acid 10 to about amino acid 20, from about amino acid 20 to about amino acid 30, or from about amino acid 30 to about amino acid 40, or a fragment of any size from about amino acid 1 to about amino acid 45 of an immunodeficiency virus Tat protein. A subject acetylated Tat polypeptide can be formulated together with one or more polypeptides comprising an amino acid sequence from about amino acid 55 to about amino acid 72, e.g., from about amino acid 55 to about amino acid 60, from about amino acid 55 to about amino acid 65, or from about amino acid 60 to about amino acid 72 of an immunodeficiency virus Tat protein. Thus, in some embodiments, a subject composition comprises at least a first acetylated Tat polypeptide; and a second polypeptide comprising-a sequence of amino acid 1 to amino acid 45 and/or amino acids 55 to about amino acid 72 of a Tat polypeptide.

A non-limiting examples, a subject acetylated Tat polypeptide can be formulated together with one or more of the following polypeptides:

Met-Glu-Pro-Val-Asp-Pro-Ser-Leu-Glu-Pro (SEQ ID NO:28);

Met-Glu-Pro-Val-Asp-Pro-Ser-Leu-Glu-Pro-Trp-Lys-His-Pro-Gly (SEQ ID NO:29);

Met-Glu-Pro-Val-Asp-Pro-Ser-Leu-Glu-Pro-Trp-Lys-His-Pro-Gly-Ser-Gln-Pro-Lys-Thr (SEQ ID NO:30);

Pro-Ser-Leu-Glu-Pro-Trp-Lys-His-Pro-Gly-Ser-Gln-Pro-Lys-Thr (SEQ ID NO:31)

Pro-Ser-Leu-Glu-Pro-Trp-Lys-His-Pro-Gly-Ser-Gln-Pro-Lys-Thr-Ala-Cys-Asn-Asn-Cys (SEQ ID NO:32);

Trp-Lys-His-Pro-Gly-Ser-Gln-Pro-Lys-Thr-Ala-Cys-Asn-Asn-Cys-Tyr-Cys-Lys-Arg-Cys (SEQ ID NO:33);

Ser-Gln-Pro-Lys-Thr-Ala-Cys-Asn-Asn-Cys-Tyr-Cys-Lys-Arg-Cys (SEQ ID NO:34);

Ser-Gln-Pro-Lys-Thr-Ala-Cys-Asn-Asn-Cys-Tyr-Cys-Lys-Arg-Cys-Cys-Phe-His-Cys-Gln (SEQ ID NO:35);

Ala-Cys-Asn-Asn-Cys-Tyr-Cys-Lys-Arg-Cys-Cys-Phe-His-Cys-Gln-Val-Cys-Phe-Ile-Lys (SEQ ID NO:36); and Tyr-Cys-Lys-Arg-Cys-Cys-Phe-His-Cys-Gln-Val-Cys-Phe-Ile-Lys-Lys-Gly-Leu-Gly-Ile (SEQ ID NO:37).

Antibody Compositions

The present invention also provides antibodies that specifically bind to a subject acetylated Tat protein. A subject antibody is useful in therapeutic methods of the invention, e.g., when administered to an individual infected with an immunodeficiency virus, a subject antibody reduces entry of an acetylated Tat protein into a cell, and inhibits transactivation of an immunodeficiency virus in the cell. A subject antibody is also useful to detect acetylated Tat protein in a biological sample. Antibodies include naturally-occurring antibodies, artificial antibodies, intrabodies, antibody fragments, and the like, that specifically bind a subject-acetylated Tat polypeptide.

In many embodiments, a subject antibody binds specifically to native Tat protein, e.g., to native acetylated Tat protein present in vivo in an individual infected with an immunodeficiency virus such as HIV-1.

In many embodiments, a subject antibody is isolated, e.g., is in an environment other than its naturally-occurring environment. In some embodiments, a subject antibody is synthetic. Suitable antibodies are obtained by immunizing a host animal with peptides comprising all or a portion of the subject protein. Suitable host animals include mouse, rat, sheep, goat, hamster, rabbit, etc. The host animal is any mammal that is capable of mounting an immune response to an acetylated Tat protein, where representative host animals include, but are not limited to, e.g., rabbits, goats, mice, etc.

The immunogen may comprise the complete protein, or fragments and derivatives thereof. Preferred immunogens comprise all or a part of the protein. Immunogens are produced in a variety of ways known in the art, e.g., expression of cloned genes using conventional recombinant methods, followed by in vitro acetylation; acetylation of a Tat protein in a cell; preparation of fragments of a subject acetylated Tat protein using well-known methods, etc.

In some embodiments, a subject antibody is bound to a solid support or an insoluble support. Insoluble supports include, but are not limited to, beads (including plastic beads, magnetic beads, and the like); plastic plates (e.g., microtiter plates); membranes (e.g., polyvinyl pyrrolidone, nitrocellulose, and the like); and the like.

For preparation of polyclonal antibodies, the first step is immunization of the host animal with the target protein, where the target protein will preferably be in substantially pure form, comprising less than about 1% contaminant. The immunogen may comprise the complete target protein, fragments or derivatives thereof. To increase the immune response of the host animal, the target protein may be combined with an adjuvant, where suitable adjuvants include alum, dextran, sulfate, large polymeric anions, oil & water emulsions, e.g. Freund's adjuvant, Freund's complete adjuvant, and the like. The target protein may also be conjugated to a carrier, e.g., KLH, BSA, a synthetic carrier protein, and the like. A variety of hosts may be immunized to produce the polyclonal antibodies. Such hosts include rabbits, guinea pigs, rodents, e.g. mice, rats, sheep, goats, and the like. The target protein is administered to the host, e.g., intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. The antibody may be purified from the hybridoma cell supernatants or ascites fluid by conventional techniques, e.g. affinity chromatography using protein bound to an insoluble support, protein A sepharose, etc.

The antibody may be produced as a single chain, instead of the normal multimeric structure. Single chain antibodies are described in Jost et al. (1994) *J. Biol. Chem.* 269:26267-73, and elsewhere. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Also provided are "artificial" antibodies, e.g., antibodies and antibody fragments produced and selected in vitro. In some embodiments, such antibodies are displayed on the surface of a bacteriophage or other viral particle. In many embodiments, such artificial antibodies are present as fusion proteins with a viral or bacteriophage structural protein, including, but not limited to, M13 gene III protein. Methods of producing such artificial antibodies are well known in the art. See, e.g., U.S. Pat. Nos. 5,516,637; 5,223,409; 5,658,727; 5,667,988; 5,498,538; 5,403,484; 5,571,698; and 5,625,033.

Also of interest are humanized antibodies. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) *Proc. Natl. Acad. Sci. USA.* 84:3439 and (1987) *J. Immunol.* 139: 3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91-3242. Human C region genes are readily available from known clones. The choice of isotype will be guided by the desired effector functions, such as complement fixation, or activity in antibody-dependent cellular cytotoxicity. Exemplary isotypes are IgG1, IgG3 and IgG4. Either of the human light chain constant regions, kappa or lambda, may be used. The chimeric, humanized antibody is then expressed by conventional methods. Other methods for preparing chimeric antibodies are described in, e.g., U.S. Pat. No. 5,565,332.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, BACs, EBV-derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral long terminal repeats (LTsS) and other promoters, e.g. SV-40 early promoter, (Okayama et al. (1983) Mol. Cell. Bio. 3:280), Rous sarcoma virus LTR (Gorman et al. (1982) *Proc. Natl. Acad. Sci. USA* 79:6777), and moloney murine leukemia virus LTR (Grosschedl et al. (1985) *Cell* 41:885); native Ig promoters, etc.

Intrabodies that specifically bind acetylated Tat are expressed in a cell in an individual, where they neutralize acetylated Tat intracellularly. See, e.g., Marasco et al. (1999) *J. Immunol. Methods* 231:223-238. Intracellularly expressed antibodies, or intrabodies, are single-chain antibody molecules designed to specifically bind and inactivate target molecules inside cells. See, e.g., Chen et al., Hum. Gen. Ther. (1994) 5:595-601; Hassanzadeh et al., Febs Lett. (1998) 16 (1, 2):75-80 and 81-86; Marasco (1997) *Gene Ther.* 4:11-15; and "Intrabodies: Basic Research and Clinical Gene Therapy Applications" W. A. Marasco, eg., (1998) Springer-Verlag, NY. Inducible expression vectors can be constructed that encode intrabodies that bind specifically to acetylated Tat protein. These vectors are introduced into an individual, and production of the intrabody induced by administration to the individual of the inducer. Alternatively, the expression vector encoding the intrabody provides for constitutive production of the intrabody.

A subject antibody may be labeled, directly or indirectly. Suitable labels include radioisotopes; enzymes whose products are detectable (e.g., luciferase, β-galactosidase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin, aequorin (a green fluorescent protein), and the like.

Suitable detectable moieties include, but are not limited to, fluorescent, metallic, enzymatic and radioactive markers such as fluorescent proteins, biotin, gold, ferritin, alkaline phosphatase, β-galactosidase, luciferase, horse radish peroxidase, peroxidase, urease, fluorescein, rhodamine, tritium, $^{14}$C, and iodination. The binding agent, e.g., an antibody, can be used as a fusion protein, where the fusion partner is a fluorescent protein. Fluorescent proteins include, but are not limited to, a green fluorescent protein from Aequoria Victoria or a mutant or derivative thereof e.g., as described in U.S. Pat. Nos. 6,066,476; 6,020,192; 5,985,577; 5,976,796; 5,968,750; 5,968,738; 5,958,713; 5,919,445; 5,874,304; e.g., Enhanced GFP, many such GFP which are available commercially, e.g., from Clontech, Inc.; any of a variety of fluorescent and colored proteins from Anthozoan species, as described in, e.g., Matz et al. (1999) *Nature Biotechnol.* 17:969-973; and the like.

In some embodiments, the antibodies are formulated in a composition with a pharmaceutically acceptable excipient. Subject antibodies formulated with a pharmaceutically acceptable excipient are useful for administering to an individual infected with an immunodeficiency virus, e.g., HIV-1, where the subject antibodies bind specifically to acetylated Tat in the serum, thereby reducing entry of acetylated Tat into a cell. Thus, a subject antibody is useful in a method of reducing transcriptional activation of HIV-1 in an individual.

Methods of Use of an Acetylated Tat Polypeptide

The present invention provides methods of inducing an immune response to an immunodeficiency virus Tat protein in an individual; methods of reducing the level of acetylated Tat protein in the serum of an individual; and methods of inhibiting transcriptional activation of an immunodeficiency virus in a cell of an individual, where the individual is infected with an immunodeficiency virus, or is at risk of being infected with an immunodeficiency virus. In some embodiments, the methods involve administering an acetylated Tat protein to an individual in need thereof in an amount effective to induce an immune response to the Tat protein. In many embodiments, the Tat protein is an HIV-1 Tat protein, and the individual is infected with, or is at risk of being infected with, HIV-1. A subject acetylated Tat protein is also useful for the production of anti-acetylated Tat antibodies, as described above. In other embodiments, the methods involve administering an anti-acetylated Tat antibody to an individual in need thereof, in an amount effective to reduce the serum level of acetylated Tat polypeptide and/or in an amount effective to reduce entry of acetylated Tat polypeptide into a cell of the individual, thereby reducing the level of transcriptional activation of an immunodeficiency virus in a cell of the individual.

Formulations, Dosages, and Routes of Administration

In some embodiments, an effective amount of an acetylated Tat protein is administered. In general, effective amount of an acetylated Tat polypeptide is an amount that is effective to elicit a detectable immune response to acetylated Tat protein present in the individual in one or more dosing events. In some embodiments, an acetylated Tat protein elicits an antibody (humoral) response. In other embodiments, an acetylated Tat protein elicits a cellular immune response, e.g., cytotoxic T lymphocytes specific for acetylated Tat protein are produced in response to administration of the acetylated Tat protein. In other embodiments, both a humoral and a cellular immune response are elicited in response to administration of the acetylated Tat protein. In some embodiments, a systemic immune response is induced. In other embodiments, a mucosal immune response is induced. In other embodiments, both a systemic and a mucosal immune response are induced.

In some embodiments, an effective amount of an acetylated Tat protein is an amount that is effective to reduce entry of acetylated Tat into a cell by at least about 10%, at least about 20%, at least about 30%, at least about 40%, at least about 50%, at least about 60%, at least about 70%, at least about 80%, or more, compared to the amount of acetylated Tat that enters the cell in the absence of administration of the acetylated Tat protein.

In some embodiments, an effective amount of an acetylated Tat protein is an amount that is effective to reduce viral load in an individual by at least about 10%, at least about 20%, at least about 30%, at least about 40%, at least about 50%, at least about 60%, at least about 70%, at least about 80%, or more, compared to the viral load in the individual in the absence of treatment with the acetylated Tat protein.

In some embodiments, an effective amount of an acetylated Tat protein is an amount that is effective to reduce serum acetylated Tat levels in an individual by at least about 10%, at least about 20%, at least about 30%, at least about 40%, at least about 50%, at least about 60%, at least about 70%, at least about 80%, or more, compared to the serum level of acetylated Tat in the individual in the absence of treatment with the acetylated Tat protein.

In some embodiments, an effective amount of an acetylated Tat protein is an amount that is effective to reduce the level of transcription of an immunodeficiency virus in an infected cell (e.g., in a cell infected with the immunodeficiency virus) in an individual by at least about 10%, at least about 20%, at least about 30%, at least about 40%, at least about 50%, at least about 60%, at least about 70%, at least about 80%, or more, compared to the level of transcription of the immunodeficiency virus in an infected cell in the individual in the absence of treatment with the acetylated Tat protein.

In general, an acetylated Tat polypeptide is administered in an amount of from about 1 μg to about 500 μg per dosing event, e.g., from about 1 μg to about 10 μg, from about 10 μg to about 20 μg, from about 20 μg to about 30 μg, from about 30 μg to about 40 μg, from about 40 μg to about 50 μg, from about 50 μg to about 60 μg, from about 60 μg to about 70 μg, from about 70 μg to about 80 μg, from about 80 μg to about 90 μg, from about 90 μg to about 100 μg, from about 100 μg to about 200 μg, from about 200 μg to about 300 μg, from about 300 μg to about 400 μg, or from about 400 μg to about 500 μg per dosing event. The microgram quantities are based on the amount of acetylated Tat protein (e.g., not including the amount of carrier) per dosing event.

In carrying out the treatment methods of the invention, in some embodiments, a single dose is administered. In other embodiments, multiple doses of acetylated Tat polypeptide are administered. The interval at which the doses are administered can vary, depending on a variety of factors, and the interval between any given dose and the subsequent dose is from about 1 day to about 1 month or more, e.g., from about 1 day to about 2 days, from about 2 days to about 7 days, from about 7 days to about 2 weeks, from about 2 weeks to about 4 weeks, or longer.

In many embodiments, an acetylated Tat polypeptide is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid) over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or for a period of more than 4 years.

The term "dosing event" as used herein refers to administration of an agent to a patient in need thereof, which event may encompass one or more releases of an agent from a drug dispensing device.

In the subject methods, an acetylated Tat polypeptide may be administered to the host using any convenient means capable of resulting in the desired therapeutic effect. Thus, the an acetylated Tat polypeptide can be incorporated into a variety of formulations for therapeutic administration. More particularly, the an acetylated Tat polypeptide of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, an acetylated Tat polypeptide may be administered in the form of their pharmaceutically acceptable salts, or may also be used alone or in appropriate association, as well as in combination, with other pharmaceutically active compounds. The following methods and excipients are merely exemplary and are in no way limiting.

For oral preparations, an acetylated Tat polypeptide can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An acetylated Tat polypeptide can be formulated into preparations for injection by dissolving, suspending or emulsifying the protein in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Furthermore, an acetylated Tat polypeptide can be made into suppositories by mixing with a variety of bases such as emulsifying bases or water-soluble bases. The compounds of the present invention can be administered rectally via a suppository. The suppository can include vehicles such as cocoa butter, carbowaxes, and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of an acetylated Tat polypeptide of the present invention calculated in an amount sufficient to produce the desired effect in association with a pharmaceutically acceptable diluent, carrier or vehicle. The specifications for the novel unit dosage forms of the present invention depend on the particular polypeptide employed and the effect to be achieved, and the pharmacodynamics associated with each polypeptide in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

As such, administration of an acetylated Tat polypeptide can be achieved in various ways, including oral, buccal, rectal, parenteral, intraperitoneal, intradermal, subcutaneous, intravenous, intramuscular, transdermal, intratracheal, etc., administration. In some embodiments, two different routes of administration are used. For example, where the therapy is a combination therapy, one agent is administered subcutaneously, and a second agent is administered orally.

Parenteral routes of administration other than inhalation administration include, but are not necessarily limited to, topical, transdermal, subcutaneous, intramuscular, intraorbital, intraspinal, intrasternal, and intravenous routes; i.e., any route of administration other than through the alimentary canal. Parenteral administration can be carried to effect systemic or local delivery of an acetylated Tat polypeptide.

Systemic administration typically involves intravenous, intradermal, subcutaneous, or intramuscular administration or systemically absorbed topical or mucosal administration of pharmaceutical preparations. Mucosal administration includes administration to the respiratory tissue, e.g., by inhalation, nasal drops, ocular drop, etc.; anal or vaginal routes of administration, e.g., by suppositories; and the like.

Inducing a T-Cell Response

In some embodiments, the present invention provides methods of inducing a cellular immune response, e.g., a cytotoxic T lymphocyte (CTL) response, to an immunodeficiency virus Tat protein. The methods generally involve loading an acetylated Tat peptide on a dendritic cell (DC), forming a primed DC; and introducing the primed DC into the individual being treated. Methods for loading a peptide onto a DC are well known in the art, and any known method can be used. See, e.g., Tuettenberg et al. (2003) Gene Ther. 10:243-250. A DC can be pulsed with a subject acetylated Tat peptide by a peptide-pulsing method and/or by genetically modifying the DC with a construct comprising a nucleotide sequence that encodes a Tat polypeptide.

In some embodiments, the methods are carried out in vivo, e.g., the DCs are pulsed with acetylated Tat peptide in vivo. In other embodiments, the methods are carried out ex vivo, e.g., DCs are removed from an individual, and the DCs are contacted with acetylated Tat peptide in vitro. DCs that present acetylated Tat peptide on their cell surface together with MHC Class I molecules are referred to as "antigen-primed" DCs.

In many embodiments, DCs are removed from an individual, and contacted in vitro with soluble acetylated Tat peptide. In some embodiments; the DCs are from DC precursors (e.g., DCs from bone marrow precursors, from $CD14^+$ precursors, from $CD34^+$ precursors etc.). In some embodiments, the DCs are mature DCs. In other embodiments, the DCs are immature DCs. In still other embodiments, the DCs are a mixture of mature and immature DCs. DC precursors can be induced to mature by culturing in the presence of factors such as GM-CSF and IL-4. Human DCs may be defined as $CD4^+$ $HLA-DR^+$ $lin^-$ (CD3, CD14, CD19, CD56).

Suitable tissue sources for DCs include spleen, afferent lymph, bone marrow, and blood, including peripheral blood, fetal blood, and umbilical cord blood. The tissue source may be treated prior to culturing to enrich the proportion of DCs relative to other cell types. The method of treatment may depend on the particular tissue source. For example, spleen or bone marrow would be treated so as to separate leukocytes from other cell types. Treatment of blood would involve cell separation techniques to separate leukocytes from other cells types including red blood cells (RBCs). Removal of RBCs may be accomplished by standard methods known to those skilled in the art. Where bone marrow is used as the tissue source, B cells and granulocytes are removed prior to culturing of bone marrow. Those skilled in the art are familiar with methods of isolating DCs from tissues. See, e.g., U.S. Pat. No. 6,194,204. Kits for isolating DCs are commercially available and can be used to obtain DCs for use in the instant invention. StemSep™ is an example of a DC isolation kit.

"Isolated" DCs suitable for use herein are generally at least about 50%, at least about 60%, at least about 70%, at least about 75%, at least about 80%, at least about 85%, at least about 90%, at least about 95%, or at least about 99%, pure, e.g., free of other, non-dendritic cells.

In some embodiments, the antigen-primed DC is live and is capable of undergoing mitosis. In other embodiments, the antigen-primed DC is dead, or is live but incapable of undergoing mitosis, and is intact. In some of these embodiments, the antigen-primed DC is irradiated. In some embodiments, the antigen-primed DC is derived from the individual being treated, e.g., is autologous. For example, DC are isolated from an individual being treated, pulsed with a subject actetylated Tat peptide, and the pulsed DC are administered to the individual, where they stimulate an immune response to Tat polypeptide.

In other embodiments, the antigen-primed DC is derived from an individual other than the recipient individual being treated, e.g., the antigen-primed DC is from a non-autologous donor. In some of these embodiments, the donor antigen-primed DC is MHC matched (e.g., HLA matched) to the recipient. In other embodiments, the donor antigen-primed DC is not HLA matched to the recipient.

In some embodiments, from about $10^3$ to about $5 \times 10^3$, from about $5 \times 10^3$ to about $10^4$, from about $10^4$ to about $5 \times 10^4$, from about $5 \times 10^4$ to about $10^5$, from about $10^5$ to about $5 \times 10^5$, from $5 \times 10^5$ to about $10^6$, from about $10^6$ to about $5 \times 10^6$, from about $5 \times 10^6$ to about $10^7$, or from about $10^7$ to $5 \times 10^7$ antigen-primed DCs are introduced into the individual.

Determining Efficacy

Any of a variety of methods can be used to determine whether a treatment method is effective. Whether antibody specific for acetylated Tat protein is elicited in response to administration of the acetylated Tat protein is readily determined using any of a variety of well-known immunological assays, including, but not limited to an enzyme-linked immunosorbent assay (ELISA); a radioimmunoassay (RIA); a protein blot assay (e.g., wherein serum samples are separated electrophoretically on a gel, transferred to a membrane, and probed with labeled acetylated Tat protein for the presence of specific antibodies); and the like.

Whether a CTL response specific for an acetylated Tat protein is elicited in response to administration of the acetylated Tat protein is readily determined using any of a number of well-established assays. Suitable assays include, but are not limited to, measuring specific lysis by CTL of target cells expressing antigen (e.g., acetylated Tat protein or epitope) on their surface, which target cells have incorporated a detectable label which is released from target cells upon lysis, and can be measured, using, e.g., any known assay, e.g., a $^{51}$Cr-release assay, a lanthanide fluorescence-based cytolysis assay, and the like.

Whether the serum level of acetylated Tat polypeptide is reduced can be determined using any standard immunological assay (e.g., ELISA, RIA, protein blot, etc.), and an antibody specific for acetylated Tat polypeptide.

Methods of determining whether the methods of the invention are effective in treating an immunodeficiency virus infection, are any known test for indicia of immunodeficiency virus infection, including, but not limited to, measuring viral load, e.g., by measuring the amount of immunodeficiency virus in a biological sample, e.g., using a polymerase chain reaction (PCR) with primers specific for an immunodeficiency virus polynucleotide sequence; detecting and/or measuring a polypeptide encoded by an immunodeficiency virus, e.g., p24, gp120, reverse transcriptase, using, e.g., an immunological assay with an antibody specific for the polypeptide; and measuring CD4 cell count in the individual. Methods of assaying an immunodeficiency virus infection (or any indicia associated with an immunodeficiency virus infection) are known in the art, and have been described in numerous publications such as HIV Protocols (Methods in Molecular Medicine, 17) N. L. Michael and J. H. Kim, eds. (1999) Humana Press.

Combination Therapies

In some embodiments, a subject acetylated Tat polypeptide is administered to an individual in combination (e.g., in the same formulation or in separate formulations) with one or more additional therapeutic agents ("combination therapy"). The subject acetylated Tat polypeptide can be administered in admixture with another therapeutic agent or can be administered in a separate formulation. When administered in separate formulations, a subject acetylated Tat polypeptide and an additional therapeutic agent can be administered substantially simultaneously (e.g., within about 60 minutes, about 50 minutes, about 40 minutes, about 30 minutes, about 20 minutes, about 10 minutes, about 5 minutes, or about 1 minute of each other) or separated in time by about 1 hour, about 2 hours, about 4 hours, about 6 hours, about 10 hours, about 12 hours, about 24 hours, about 36 hours, or about 72 hours, or more.

Therapeutic agents that can be administered in combination with an effective amount of an agent that inhibits one or more immunodeficiency virus functions, which functions include, but are not limited to, viral replication; viral protease activity; viral reverse transcriptase activity; viral entry into a cell; viral integrase activity; activity of one or more of Rev, Tat, Nef, Vpr, Vpu, and Vif; and the like.

Therapeutic agents that can be administered in combination therapy with a subject acetylated Tat polypeptide include, but are not limited to, anti-inflammatory agents, anti-viral agents, anti-fungal agents, anti-mycobacterial agents, antibiotics, amoebicidal agents, trichomonocidal agents, analgesics, anti-neoplastic agents, anti-hypertensives, anti-microbial agents, or combinations of the foregoing.

In some embodiments, patients with an immunodeficiency virus infection are treated with a combination of one or more acetylated Tat polypeptides with one or more of the following: beta-lactam antibiotics, tetracyclines, chloramphenicol, neomycin, gramicidin, bacitracin, sulfonamides, nitrofurazone, nalidixic acid, cortisone, hydrocortisone, betamethasone, dexamethasone, fluocortolone, prednisolone, triamcinolone, indomethacin, sulindac, acyclovir, amantadine, rimantadine, recombinant soluble CD4 (rsCD4), a fusion inhibitor (e.g., a T20 peptide, a T-1249 peptide; Trimeris); an anti-CD4 antibody (e.g., an anti-CD4 antibody from Tanox, Inc.); an anti-CCR5 antibody (e.g., Pro 140); a CXCR4 blocker (e.g., AMD 3100); an HIV entry inhibitor (e.g., Pro-542; Progenics); a CCR5 blocker (e.g., SCH-C, SCH-D; Schering Plough); anti-receptor antibodies (e.g., for rhinoviruses), nevirapine (Viramune®), emiravine (Coactinon®), cidofovir (Vistide™), trisodium phosphonoformate (Foscarnet™), famcyclovir, pencyclovir, valacyclovir, nucleic acid/replication inhibitors, interferon, zidovudine (AZT, Retrovir™), didanosine (dideoxyinosine, ddI, Videx™), stavudine (d4T, Zerit™), zalcitabine (dideoxycytosine, ddC, Hivid™), nevirapine (Viramune™), lamivudine (Epivir™, 3TC), protease inhibitors, saquinavir (Invirase™, Fortovase™), ritonavir (Norvir™), nelfinavir (Viracept™), efavirenz (Sustiva™), abacavir (Ziagen™), amprenavir (Agenerase™) indinavir (Crixivan™), ganciclovir, AzDU, delavirdine (Rescriptor™), kaletra, trizivir, rifampin, clarithromycin, erythropoietin, colony stimulating factors (G-CSF and GM-CSF), non-nucleoside reverse transcriptase inhibitors, nucleoside reverse transcriptase inhibitors, HIV protease inhibitors, adriamycin, fluorouracil, methotrexate, asparaginase and combinations thereof.

For example, a subject acetylated Tat protein is administered in combination therapy with one or more nucleoside reverse transcriptase inhibitors (RTI's; where nucleoside reverse transcriptase inhibitors include AZT, ddI, 3TC, ddC, d4T, and abacavir); and/or one or more protease inhibitors (where protease inhibitors include indinavir, saquinavir, ritonavir, nelfinavir, amprevanir, and lopinavir); and/or one or more non-nucleoside reverse transcriptase inhibitors (where non-nucleoside reverse transcriptase inhibitors include nevirapine, delavirdine, emiravine, and efavirenz); and/or a fusion inhibitor (e.g., T20, T-1249); and/or a CCR5 blocker (e.g., SCH-C, SCH-D).

A subject acetylated Tat protein can be administered to an individual in combination with any highly active antiretroviral therapy (HAART) or Structured Treatment Interruptions (STI) regimen currently in use.

Methods of Use of a Subject Antibody

A subject antibody is useful in both therapeutic and diagnostic applications. Therapeutic methods generally involve administering to an individual in need thereof an effective amount of a subject antibody. The administered antibody binds specifically to acetylated Tat protein, and reduces entry of acetylated Tat protein into a cell. Reducing entry of an acetylated Tat protein into a cell reduces the level of production of the immunodeficiency virus in the cell.

Therapeutic Applications

For therapeutic applications, a subject antibody is formulated in a composition that comprises a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", 19$^{th}$ Ed. (1995), or latest edition, Mack Publishing Co; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

The amount of antibody that is administered depends on various factors, such as the weight of the individual, the immunological status of the individual, the severity of disease, and the like, which factors are readily determined by trained medical personnel. In general, an effective amount of a subject antibody is administered to an individual, where an effective amount is one or more doses of antibody that are effective to reduce the level of acetylated Tat in the serum by at least about 10%, at least about 20%, at least about 30%, at least about 40%, at least about 50%, at least about 60%, at least about 70%, at least about 80%, or more, compared to the level of acetylated Tat in the serum of the individual not treated with the antibody.

Suitable routes of administration of a subject antibody include oral, buccal, rectal, parenteral, intraperitoneal, intradermal, subcutaneous, intravenous, intramuscular, transdermal, intratracheal, etc., administration.

Whether a subject method is effective in reducing the level of acetylated Tat can be determined using any known assay, e.g., an ELISA, an RIA, a protein blot, and the like.

Diagnostic Applications

A subject antibody is also useful for detecting the presence of and/or determining the level of acetylated Tat in a biological sample, e.g., a biological sample taken from an individual being tested for the presence and/or level of acetylated Tat. As used herein, the terms "detecting" and "determining" refer to both quantitative and qualitative determinations and as such, the term "determining" is used interchangeably herein with "assaying," "measuring," and the like.

In general, a subject assay for detecting an acetylated Tat protein in a biological sample involves contacting a biological sample with an antibody that specifically binds acetylated Tat, and detecting binding of the antibody to the sample.

The screening methods may be designed a number of different ways, where a variety of assay configurations and protocols may be employed, as are known in the art. For example, one of the components may be bound to a solid support, and the remaining components contacted with the support bound component. The above components of the method may be combined at substantially the same time or at different times.

A variety of other reagents may be included in the assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The components of the assay mixture are added in any order that provides for the requisite binding or other activity. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

Following the contact and incubation steps, the subject methods will generally, though not necessarily, further include a washing step to remove unbound components, where such a washing step is generally employed when required to remove label that would give rise to a background signal during detection, such as radioactive or fluorescently labeled non-specifically bound components. Following the optional washing step, the presence of bound complexes will then be detected.

Detection of specific binding of the acetylated Tat-specific antibody, when compared to a suitable control, is an indication that acetylated Tat polypeptides are present in the sample. Suitable controls include a sample known not to contain an acetylated Tat polypeptide; and a sample contacted with an antibody not specific for acetylated Tat, e.g., an anti-idiotype antibody. A variety of methods to detect specific antibody-antigen interactions are known in the art and can be used in the method, including, but not limited to, standard immunohistological methods, immunoprecipitation, an enzyme immunoassay, and a radioimmunoassay.

In general, the acetylated Tat-specific antibody will be detectably labeled, either directly or indirectly. Direct labels include radioisotopes; enzymes whose products are detectable (e.g., luciferase, β-galactosidase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin, aequorin (a green fluorescent protein), and the like.

The antibody may be attached (coupled) to an insoluble support, such as a polystyrene plate or a bead. Indirect labels include second antibodies specific for acetylated Tat-specific antibodies, wherein the second antibody is labeled as described above; and members of specific binding pairs, e.g., biotin-avidin, and the like. The biological sample may be brought into contact with an immobilized on a solid support or carrier, such as nitrocellulose, that is capable of immobilizing cells, cell particles, or soluble proteins. The support may then be washed with suitable buffers, followed by contacting with a detectably-labeled acetylated Tat-specific antibody. Detection methods are known in the art and will be chosen as appropriate to the signal emitted by the detectable label. Detection is generally accomplished in comparison to suitable controls, and to appropriate standards.

In some embodiments, a biological sample is contacted in vitro with acetylated Tat that is coupled to a bead, and bound antibody is detected using a fluorescence activated cell sorter. Antibody bound to the bead-bound acetylated Tat is detected using a fluorescently labeled binding agent that binds to the bound antibody. Suitable fluorescently-labeled binding agents include a second antibody that binds the anti-acetylated Tat antibody; protein A; and the like.

Subjects Suitable for Treatment

The methods of the present invention are suitable for treating individuals who have an immunodeficiency virus infection. Such individuals include those who have been diagnosed as having an HIV infection.

In some cases, the individual is $CD4^+$ deficient, or $CD4^+$ low. The terms "$CD4^+$-deficient" and "$CD4^+$-low" are used interchangeably herein, and, as used herein, refer to a state of an individual in whom the number of $CD4^+$ T lymphocytes is reduced compared to an individual with a healthy, intact immune system. $CD4^+$ deficiency includes a state in which the number of functional $CD4^+$ T lymphocytes is less than about 600 $CD4^+$ T cells/$mm^3$ blood; a state in which the number of functional $CD4^+$ T cells is reduced compared to a healthy, normal state for a given individual; and a state in which functional $CD4^+$ T cells are completely absent. As used herein, a "$CD4^+$-deficient individual" is one who has a reduced number of functional $CD4^+$-T cells, regardless of the reason, when compared to an individual having a normal, intact immune system. In general, the number of functional $CD4^+$-T cells that is within a normal range is known for various mammalian species.

Also suitable for treatment with a subject method are individuals who are at risk of contracting an immunodeficiency virus infection. Such individuals include, but are not limited to, individuals with healthy, intact immune systems, but who are at risk for becoming HIV infected ("at-risk" individuals). At-risk individuals include, but are not limited to, individuals who have a greater likelihood than the general population of becoming HIV infected. Individuals at risk for becoming HIV infected include, but are not limited to, individuals at risk for HIV infection due to sexual activity with HIV-infected individuals; intravenous drug users; individuals who may have been exposed to HIV-infected blood, blood products, or other HIV-contaminated body fluids; babies who are being nursed by HIV-infected mothers.

Also suitable for treatment with a subject method are individuals who were treated for an immunodeficiency virus infection, but who relapsed, e.g., whose $CD4^+$ T cell count was increasing in response to anti-viral therapy for HIV, but whose $CD4^+$ T cell counts subsequently began to fall.

The methods of the present invention are suitable for treating individuals who failed treatment with previous anti-viral therapy for the treatment of an HIV infection. ("treatment failure patients"). Such treatment failure patients include individuals who have undergone previous HAART or STI treatment regimens.

Also suitable are individuals who were previously treated with anti-retroviral therapy for the treatment of an HIV infection, and in whom drug-resistant HIV has emerged.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s, second(s); min, minute(s); hr, hour(s); ng, nanogram; and the like.

Example 1

Acetylated HIV Tat Protein

Experimental Procedures

Preparation and Use of Monoclonal and Polyclonal Antibodies

Chemically synthesized $K_{50}$-acetylated ARM peptides (SYGRK(AC)KRRQRC; SEQ ID NO:03) were conjugated to keyhole limpet hemocyanin (KLH; Pierce, Rockford, Ill.), mixed with complete Freund's adjuvant (Sigma, St. Louis, Mo.), and injected into rabbits. Four boosts were performed with incomplete Freund's adjuvant in rabbits. Monoclonal antibodies (clone TALT5.24) were generated with the same immunogen according to a rapid repetitive immunization protocol (Bynum et al. (1999) Hybridoma 18, 407-411). Immunoglobulin G were purified on Gammabind Plus Sepharose (Amersham). For ELISA, polystyrene plates were coated overnight at 4° C. with 100 ng of Tat or AcTat protein per mL carbonate buffer (500 mM $NaHCO_3$). Plates were incubated with IgGs in milk and developed with horseradish peroxidase-conjugated secondary antibodies (Jackson ImmunoResearch Laboratories) and 5 mg/ml o-phenylenediamine (Sigma). Immunoprecipitations of the FLAG-Tat protein were performed with 10 μg/ml M2 monoclonal antibody (Sigma) as previously described (Ott et al. (1999) Curr Biol 9, 1489-1492). For western blotting with polyclonal α-AcARM IgGs, 0, 0.3, 1, 3, 10, 30, 100 ng of synthetic Tat proteins were loaded, for analysis with monoclonal α-AcARM IgGs, 0, 0.5, 1, 2 μg of each protein were loaded. AcTat concentrations in blocking experiments were 125, 250, 500 ng/lane for the monoclonal, and 31, 62, 125 ng/lane for the polyclonal antibody.

CHIP Assays

Both GFP- and Tat-transduced Jurkat cells were fixed for 10 min with 1% formaldehyde. Soluble chromatin was prepared and purified by cesium chloride isopicnic centrifugation as previously described (Orlando et al. (1997). Methods 11, 205-214). Precleared chromatin solutions were incubated overnight at 4° C. with 5 μl of the antibody (rabbit α-AcARM IgGs). Immune complexes were collected with protein A-agarose preblocked with sonicated salmon sperm DNA (Upstate Biotechnology). Formaldehyde cross-links were reverted by incubating the samples at 65° C. overnight in the presence of 200 mM NaCl. One-tenth of the immunoprecipitated DNA was used in PCR reactions using the following primer pair for HIV LTR detection (5'-TTGCCTG-TACTGGGTCTCTCTG-3' (SEQ ID NO:38) and 5'-TCGCTTTCAGGTCCCTGTTCG-3' (SEQ ID NO:39) and the following pair for c-fos detection (5'-TGCATA-GAAGGACCCAGATAGGTC-3' (SEQ ID NO:40) and 5'-TCAATGACCCTGAGCCCAAG-3' (SEQ ID NO:41)).

Synthetic Tat Proteins

Solid-phase peptide synthesis of 72-amino acid Tat was performed with a sequence derived from the isolate HIV-1$_{BRU}$ by standard Fmoc-Strategy as previously described (Dorr et al. (2002) EMBO J. 21, 2715-2723). For biotinylated proteins, biotinylation was carried out at the last step of the synthesis. All proteins were fully deprotected with trifluoracetic acid, containing 3% triisopropylsilane and 5% water. The peptides were purified to homogeneity by reverse-phase high pressure liquid chromatography (Shimadzu Scientific Instruments Inc.). The correct molecular masses for the peptides were established by positive-ion ESI mass spectra recorded on a ion trap Finnigan LCQ mass spectrometer. We also used a 86 amino acid Tat and AcTat that was synthesized on 4-hydroxymethyl-phenoxy-methyl-copolystyrene-1% divinylbenzene preloaded resin (FMP; 0.65 mmol; Perkin Elmer, Applied Biosystem Inc., Foster City, Calif.) on an automated synthesizer (ABI 433A, Perkin Elmer, Applied Biosystems Inc.) as previously described (Peloponese (1999) *J. Biol. Chem.* 274:11473-11478).

Cells and Plasmids

HeLa cells were obtained from the American Type Culture Collection, and HeLa-Tat cells were a gift from P. Krammer (Deutsches Krebsforschungszentrum, Heidelberg). Jurkat-GFP cells and the lentiviral vectors used to generate Jurkat-Tat cells are described in (Jordan et al. (2001) Embo J 20, 1726-1738). The HIV LTR-luciferase construct was described before (Emiliani et al. (1998) *Proc Natl Acad Sci USA* 95, 2795-2800). The TAR bulge mutation was generated by complete deletion of the three-nucleotide bulge and the TAR loop mutation contained C30→A, T31→G, and G33→T mutations introduced via QuickChange site-directed mutagenesis (Stratagene, La Jolla, Calif.). The RSV LTR-luciferase construct was a gift of Heike Pöpperl (DKFZ, Heidelberg), and the CMV-GFP construct was obtained from Clontech (Palo Alto, Calif.). The 5×UAS contruct, in which 5× Gal4 binding sites were cloned upstream of the TK promoter (Puigserver et al. (1999) Science 286, 1368-1371) was a gift of Bruce Spiegelman (Harvard Medical School, Boston). GST-CyclinT1 and mutant GST-CyclinT1 plasmids were provided by Katherine Jones (Salk Institute, San Diego). The lentiviral vectors LTR-GFP and LTR-Tat-IRES-GFP vectors and the method to generate viral particles pseudotyped with VSV-G are described in (Jordan et al., 2001, supra). Both vectors are minimal non-replicative HIV-1 genomes flanked by two LTRs containing viral cis-acting sequences necessary for packaging and infection (Dull et al., 1998). Viral particles were quantified with an HIV-1 p24 ELISA assay (NEN Life Science Products Inc.).

Microinjection Experiments

Microinjection experiments were previously described (Dorr et al. (2002), supra). Microinjection was performed at room temperature with a Zeiss automated injection system (Carl Zeiss, Oberkochen, Germany). Samples were prepared as a 20111 injection mix containing the luciferase reporter constructs (100 ng/ml) and CMV-GFP (50 ng/ml) constructs in sterile water or phosphate buffer. In individual experiments α-AcARM or preimmune immunoglobulins (5 mg/ml), Lys-CoA (8 µM) or synthetic Tat (30 µg/ml) were included in the mix. Four hours after injection, cells were examined on a Zeiss Axiovert microscope to determine the number of GFP-positive cells, washed in cold phosphate buffer and stored at −70° C. for luciferase assays (Promega). The α-p24 monoclonal antibody (183-H12-5C) was used in control microinjections with α-AcARM mAbs and was obtained through the AIDS Research and Reference Reagent Program, NIH (Chesebro et al. (1992) J Virol 66, 6547-6554). For immunodepletion of rabbit α-AcARM or preimmune antibodies, immunoglobulins were incubated with biotinylated AcARM peptides prebound to streptavidin-sepharose beads (30 minutes at room temperature), centrifuged and supernatant coinjected into HeLa-Tat cells.

SiRNA Transfections

Transient transfections of siRNAs (Dharmacon Research) were performed using oligofectamine (Invitrogen). 72 hours after transfection nuclear extracts were prepared according to a rapid protocol (Osborn et al. (1989) Proc. Natl. Acad. Sci. USA 86, 2336-2340) or cells were fixed with paraformaldehyde for immunofluorescence microscopy with Cy3-conjugated α-rabbit secondary antibodies (Jackson Immunoresearch Laboratories). Antibodies α-p300 (N-15) and α-CBP (A-22, both Santa Cruz) and α-Lamin A/C polyclonal antibodies (Cell Signaling Technology Inc.) were used according to the manufacturers' recommendations. Confocal images were acquired with an Olympus BX60 microscope equipped with a Radiance 2000 confocal setup (Bio-Rad).

RNA Gel Shift Experiments

TAR RNAs were synthesized from HindIII-linearized pGEM3Zf-TAR constructs, which contained an oligonucleotide corresponding to the HIV$_{LAI}$ TAR sequence (nucleotides +17 to +44) ligated into the EcoR1-HindIII cloning sites, downstream of the T7 RNA polymerase start site. In the TARΔbulge construct, thymidine 23 was replaced with an adenosine, and the TARΔloop construct contained C30→A, T31→G, and G33→T mutation. In vitro transcription reactions were performed with the Riboprobe system (Promega, Madison, Wis.) with 1 µg of linearized plasmids and 50 µCi of $^{32}$P-CTP (20 µCi/µl; Amersham Pharmacia Biotech). Transcripts were treated with 2 U DNAse I (Promega), extracted with a phenol:chloroform mixture, and purified over a Nick column (Amersham Pharmacia Biotech). Gel mobility reactions (final volume, 16 µl) were carried out at 30° C. as described (Wei et al. (1998) Cell 92, 451-462) with 2×10$^4$ cpm TAR probes/reaction with indicated concentrations of Tat proteins and 160 ng of GST-cleaved CyclinT1 (amino acids 1-303) (Garber et al. (1998) Curr Opin Immunol 11, 460-465). RNA-binding complexes were separated on a pre-run 4% Tris-glycine gel.

GST Binding Assays

Full-length GST-CyclinT1, GST-CyclinT1C261A or GST alone were expressed in the BL21 strain of *Escherichia coli* and purified on glutathione-Sepharose beads (Amersham Pharmacia Biotech) as described (Herrmann and Rice (1993) Virology 197, 601-608). For binding assays ~1 µg of bead-coupled GST-CyclinT1, GST-CyclinT1C261A or GST alone was incubated with Tat and AcTat in 100 µl modified Buffer C for 3.5 hr at 4°. Buffer C is described in (Fujinaga et al. (1999) Proc. Natl. Acad. Sci. USA 96, 1285-1290) and was used without ZnCl$_2$ and SDS. Beads were washed three times with modified Buffer C containing 1M KCl, boiled in Laemmli buffer and supernatant was analyzed by immunoblotting using monoclonal anti-Tat antibodies (clone AC11.AE12; CPR Inc.).

RNA Polymerase II Binding

Synthetic biotinylated nonacetylated and acetylated Tat proteins were incubated for 2 hours with 50 μl 293 nuclear extracts prepared according to (Dignam et al. (1983) Methods Enzymol. 101, 582-598) in buffer conditions described in (Mavankal et al., (1996) Proc. Natl. Acad. Sci. USA 93, 2089-2094). Complexes were collected with streptavidin-sepharose beads, separated by SDS-PAGE electrophoresis and analyzed with α-RNAPII antibodies (clones H14 and 8WG16; CPR Inc) or with α-AcARM mAbs and HRP-conjugated Streptavidin (Jackson Immunoresearch Laboratories).

Results

Tat is Acetylated at K$_{50}$ In Vivo.

Modification-specific antisera have been raised against several proteins to detect unique posttranslational modifications. In particular, antisera specific for histone proteins containing unique acetylated lysines have proven extremely useful in assessing the role of acetylation in transcriptional regulation. Accordingly, a specific antiserum was raised against K$_{50}$-acetylated Tat by immunizing rabbits with a synthetic peptide corresponding to the ARM containing a single acetylated lysine at position 50 (rabbit anti-AcARM). The same peptide was injected into mice to generate monoclonal antibodies specific for K$_{50}$-acetylated Tat (anti-AcARM mAb).

FIGS. 1A-F. (FIG. 1A) Western blot of synthetic Tat and AcTat using polyclonal or monoclonal anti-AcARM immunoglobulins (each 10 μg/ml). (FIG. 1B) Western blot analysis of AcTat with polyclonal or monoclonal anti-AcARM ("α-AcARM") immunoglobulins, preincubated with a 10× molar excess of the indicated agent. (FIG. 1C) Tat (filled circles) or AcTat (open circles) was coated on ELISA plates (25 ng/well) and analyzed by ELISA at the indicated dilutions of polyclonal or monoclonal anti-AcARM immunoglobulins. (FIG. 1D) Cellular lysates obtained from Jurkat T cell lines, expressing FLAG-tagged Tat or GFP, were analyzed by western blotting with anti-AcARM monoclonal antibodies. Cells were treated with 400 nM trichostatin A (TSA) or DMSO for 16 hours. (FIG. 1E) Cellular lysates were immunoprecipitated with anti-FLAG monoclonal antibodies before western blotting with anti-AcARM or anti-FLAG monoclonal antibodies. (FIG. 1F) Chromatin immunoprecipitation assay of Tat- or GFP-expressing Jurkat cells with polyclonal anti-AcARM antibodies and primers specific for the HIV LTR or for the c-fos gene as a control.

Monoclonal and polyclonal antibodies specifically recognized a synthetic Tat protein containing a single acetylated lysine at position 50 (AcTat) and showed no reactivity against synthetic unacetylated Tat (FIG. 1A). The two antibodies also recognized Tat that had been acetylated by p300 in an in vitro acetylation reaction, confirming that p300 acetylates K$_{50}$ in Tat. Additional experiments showed no cross-reactivity with total cellular proteins, acetylated histone proteins, or unacetylated Tat at concentrations as high as 2 μg.

Figure 1B:
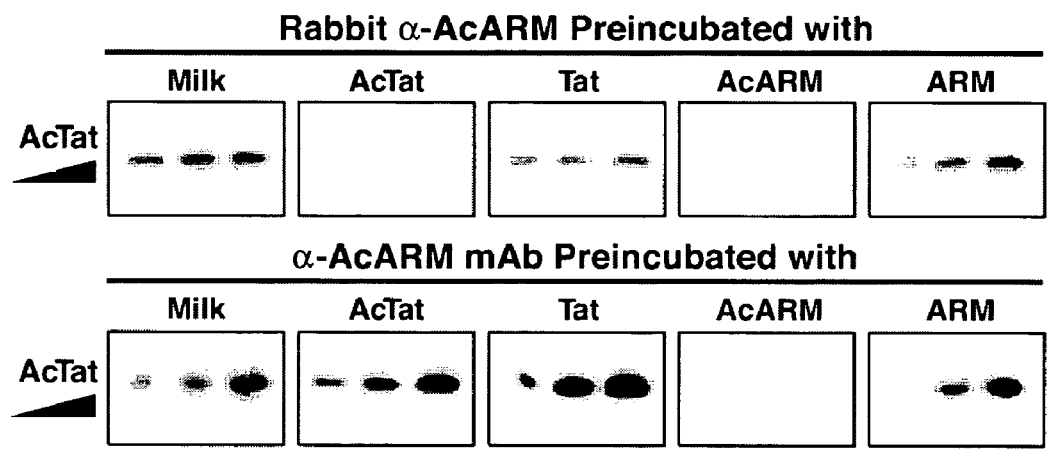
Figure 1C:
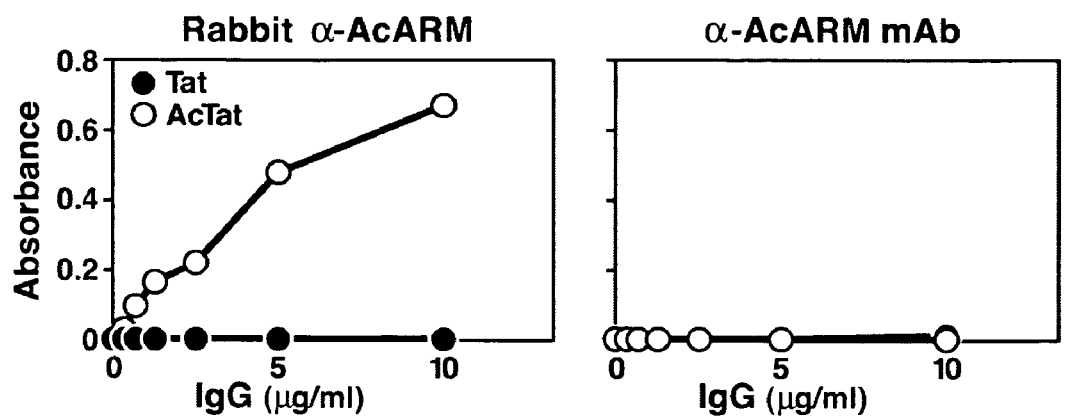

The specificity was further tested in preincubation experiments. The antibodies were preincubated with ARM peptides or synthetic Tat proteins before western blot analysis of AcTat. As expected, recognition by polyclonal and monoclonal antibodies was blocked with the acetylated ARM peptide (FIG. 1B). The unacetylated ARM peptide had no effect, confirming the specificity of both antibodies for the acetylated immunogen (FIG. 1B). Interestingly, only the polyclonal, and not the monoclonal, antibody was efficiently blocked by full-length acetylated Tat protein, indicating that both antibodies differed in their ability to recognize native, undenatured AcTat (FIG. 1B). This result was confirmed by ELISA of synthetic Tat proteins coated on polystyrene plates. Again, only the rabbit anti-AcARM antibody recognized AcTat (FIG. 1C).

Figure 1D:
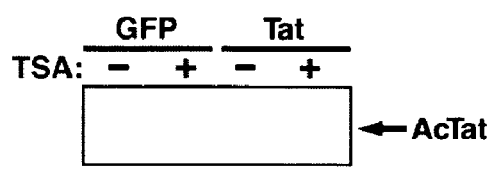
Figure 1E:
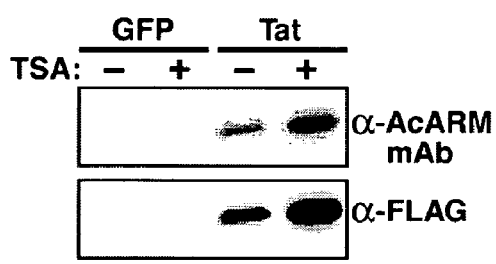

Next, cellular extracts were analyzed with anti-AcARM antibodies. A cell line was generated that constitutively expressed a FLAG-tagged Tat protein from the HIV LTR by transducing Jurkat T cells with a Tat-encoding lentiviral vector (Jordan et al., 2001, supra). Following treatment with trichostatin A (TSA), a specific inhibitor of cellular HDACs, AcTat was detected by western blot analysis with anti-AcARM mAbs in cells expressing Tat, but not in control cells expressing GFP (FIG. 1D). To enhance the signal, immunoprecipitation was performed with anti-FLAG monoclonal antibodies before western blot analysis. Again, AcTat was detected in Tat-expressing, but not in GFP control cells (FIG. 1E). Expression of AcTat was enhanced when cells were treated with TSA. However, immunodetection with anti-FLAG antibodies showed an overall upregulation of Tat expression by TSA, in agreement with the stimulatory effect of the drug on the HIV LTR.

Figure 1F:
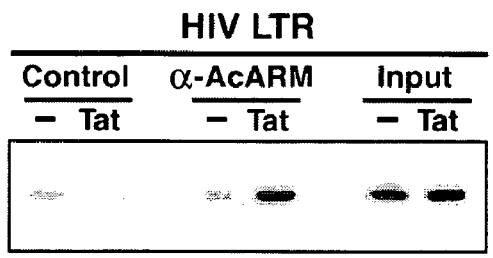
Figure 1F:
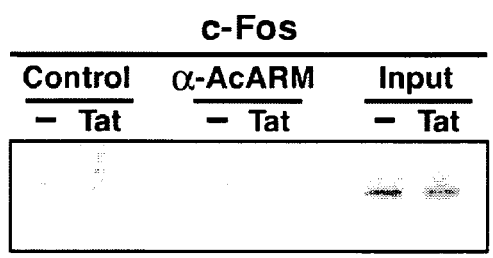

To determine whether AcTat is associated with the HIV promoter in vivo, we performed chromatin immunoprecipitation (CHIP) assays in Jurkat cells expressing Tat or GFP from integrated HIV-based lentiviral constructs. Following formaldehyde-crosslinking, solubilized chromatin was immunoprecipitated with polyclonal anti-AcARM antibodies. The DNA immunoprecipitated along with AcTat was analyzed by PCR with primers specific for the HIV LTR or for the cellular gene c-fos. In the presence of Tat, the HIV LTR sequence, and not the c-fos sequence, was enriched in the immunoprecipitated fraction, demonstrating that AcTat is specifically associated with the HIV LTR in vivo (FIG. 1F). PCR analysis of the chromatin solution before immunoprecipitation (input) confirmed that the HIV and c-fos sequences were present in equivalent amounts in both samples.

Inhibition of Tat Activity by Anti-AcARM Immunoglobulins.

Three different approaches were used to test the biological role of K$_{50}$-acetylated Tat in HIV transcription. First, the effect of anti-AcARM antibodies on Tat transactivation after nuclear microinjection was studied. HeLa cells stably expressing a full-length Tat protein (HeLa-Tat) or control HeLa cells were microinjected with an HIV LTR-luciferase construct as previously described (Dorr et al., 2002, supra). A construct expressing enhanced GFP under the control of the CMV promoter (CMV-GFP) was coinjected to assess the number and viability of injected cells before harvest.

Figure 2A:
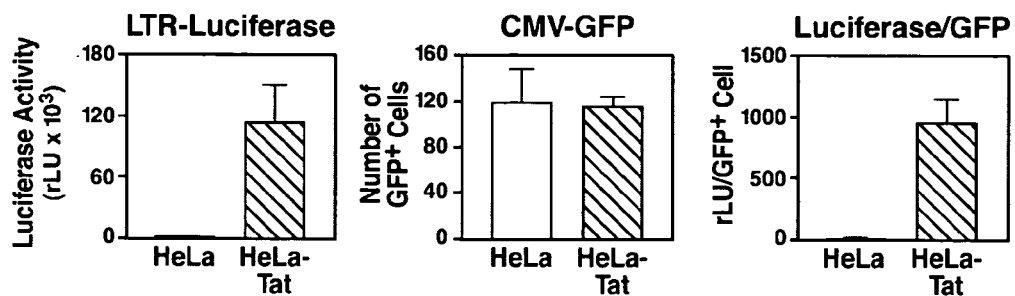
FIGS. 2A-B depict inhibition of Tat Activity by Anti-Ac-ARM Immunoglobulins or the p300-HAT Inhibitor Lys-CoA.
Figure 2B:
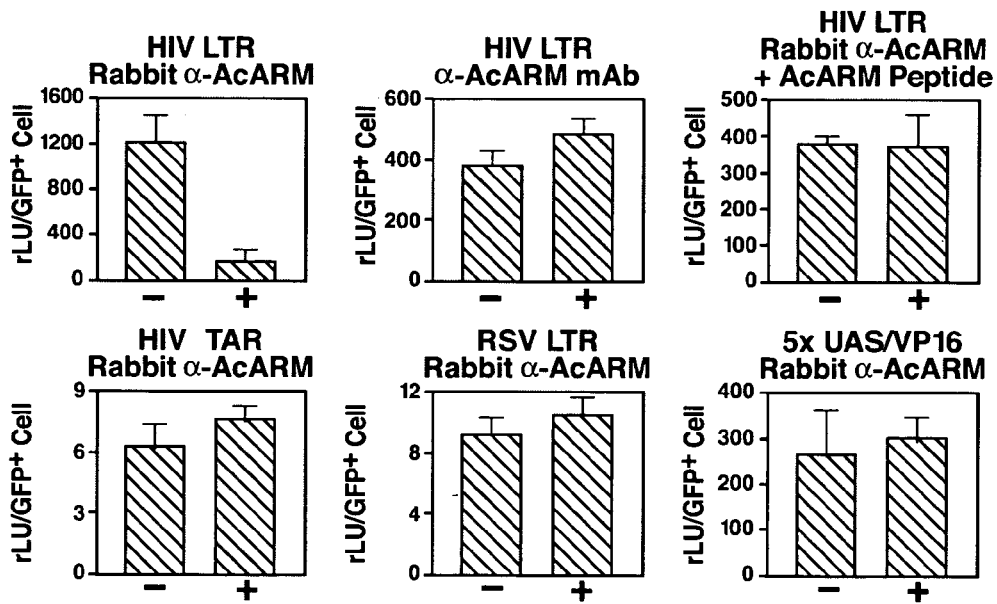

FIGS. 2A and 2B. (FIG. 2A) Microinjection of an HIV LTR-luciferase construct into HeLa or HeLa-Tat cells, stably expressing full-length Tat. A GFP-expressing construct (CMV-GFP) was coinjected to count the number of injected cells before analysis of luciferase activity. The average (±SEM) luciferase values (relative light units, rLU, left), number of GFP-positive cells (middle) and luciferase values per GFP-positive cell (right) of three independent experiments are shown. (FIG. 2B) Coinjection of anti-AcARM immunoglobulins (5 mg/ml) together with the HIV LTR-luciferase and CMV-GFP constructs into Hela-Tat cells (upper left and middle panels). Rabbit preimmune or monoclonal anti-p24 immunoglobulins were used as controls. Rabbit anti- AcARM and preimmune immunoglobulins were immunodepleted with the AcARM peptide before microinjection (upper right panel) or were coinjected with a TAR-mutant LTR-luciferase construct (lower left panel), the Tat-independent RSV LTR-luciferase construct or with the 5×UAS reporter transactivated by the Gal4-VP16 protein (lower middle and right panels). Average (±SEM) of three independent experiments is shown for each condition.

Approximately 120 cells were microinjected per condition and luciferase values were on average 200-fold higher in HeLa-Tat cells than in control HeLa cells (FIG. 2A). Coinjection of purified rabbit anti-AcARM immunoglobulins into HeLa-Tat cells inhibited Tat transactivation (>85%), whereas preimmune immunoglobulins had no effect (FIG. 2B). To validate this observation, a number of control experiments were performed (FIG. 2B). 1) In agreement with their inability to recognize native AcTat, microinjected anti-AcARM mAbs had no effect on Tat transactivation. 2) Rabbit anti-AcARM immunoglobulins, immunodepleted with AcARM peptides, showed no inhibitory effect on Tat transcriptional activity. 3) An HIV LTR reporter, carrying a TAR mutation which prevents Tat binding, also showed no inhibitory effect of the antibodies. 4) No inhibitory effect was observed on Tat-independent promoters, such as the Rous sarcoma virus (RSV) LTR or the 5×UAS reporter activated by the Gal4-VP16 transactivator. These data demonstrate that the inhibition of Tat transcriptional activity by anti-AcARM antibodies is specific, and that Tat acetylation at $K_{50}$ is necessary for Tat transcriptional activity in vivo.

p300 is a Critical Cofactor for Tat Transcriptional Activity.

Second, the effect of Lys-CoA, a recently described inhibitor of the p300 histone acetyltransferase activity, on Tat transactivation was examined.

FIGS. 3A-D. (FIG. 3A) Microinjection of the p300-HAT inhibitor Lys-CoA (8 μM), HIV LTR-luciferase and CMV-GFP into HeLa or HeLa-Tat cells. Each value is expressed as a percentage of the value obtained in control cells, injected with LTR-luciferase and CMV-GFP alone. Average (±SEM) luciferase activities (left), the corresponding number of GFP-positive cells (middle) and the ratios of luciferase values per GFP+ cell of three independent experiments are shown. (FIG. 3B) Western blot analysis of nuclear extracts prepared from HeLa cells transfected with siRNA specific for p300 or GFP. The asterix in the upper panel marks an unspecific band at ~150 kDa, in the lower panel a cleavage product of lamin A/C. (C) Microinjection experiments with HIV LTR-luciferase and CMV-GFP constructs in HeLa-Tat or HeLa cells, transfected with siRNAs specific for p300 or GL3 luciferase. HeLa cells were injected in the absence or presence of Tat (30 μg/ml). (D) HeLa cells, transfected with siRNAs specific for GL3 (filled circles) and p300 (open circles), were infected with GFP- or Tat and GFP-expressing lentiviral vectors. Transcriptional activity of the HIV LTR is measured as Mean Fluorescence Intensity (MFI) of GFP.

Figure 3A:
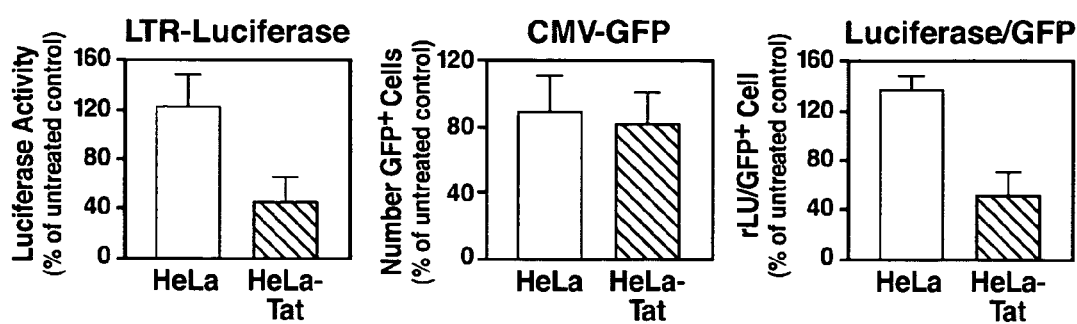
FIGS. 3A-D depict results showing that acetylation of Tat blocks the formation of the ternary Tat/TAR/CyclinT1 complex.

When microinjected into nuclei of oocytes, Lys-CoA efficiently blocked p300-dependent transcription of MyoD RNA. Pilot experiments indicated that Lys-CoA could maximally suppress Tat-mediated transactivation of the HIV promoter when injected as an 8 μM solution, which corresponds to an estimated final concentration of 0.8 to 1.6 μM in HeLa cell nuclei. In three independent experiments, Lys-CoA inhibited Tat activity on the HIV LTR by 60-70% (FIG. 3A). Lys-CoA had no effect on the coinjected CMV-GFP reporter at the same concentration. Further, Lys-CoA had no effect on the LTR alone when coinjected into HeLa cells, indicating that the p300-HAT activity targets Tat directly.

Figure 3B:
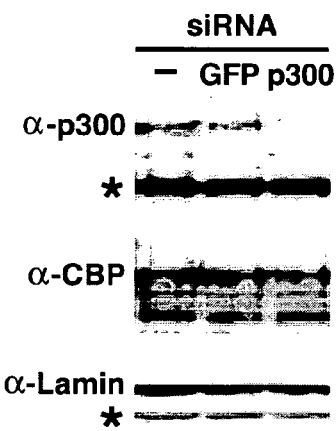

In a third approach, the critical role of p300 in Tat-mediated HIV transcription was demonstrated using short inhibitory RNA oligonucleotide duplexes (siRNA). SiRNA specific for p300 (Gronroos et al. (2002). Mol. Cell. 10, 483-493) or GFP (Novina et al. (2002) Nat. Med. 8, 681-686) were transfected into HeLa cells. Expression of p300 was monitored by western blot analysis and confocal immunofluorescence microscopy. Three days after transfection p300 expression was completely suppressed in cells transfected with siRNA specific for p300, but not for GFP (FIG. 3B). Expression of the closely related CBP protein or of Lamin A/C was unaffected by p300-siRNA.

Figure 3C:
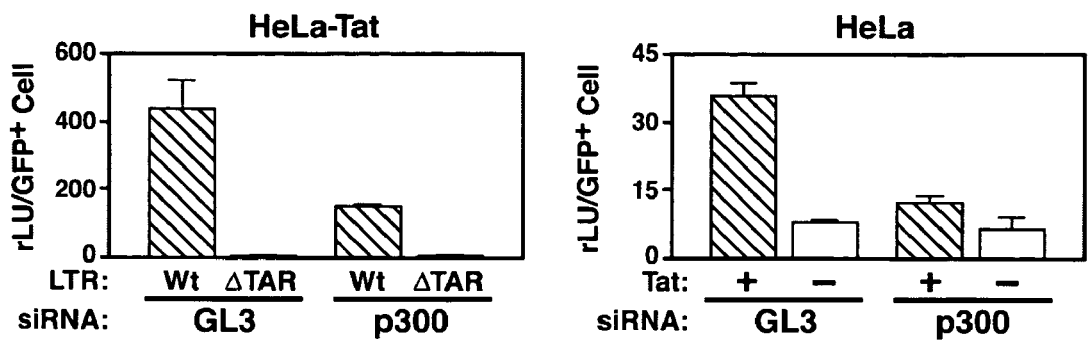

Next, the effect of the p300-siRNA on Tat transactivation was examined. Since CMV-GFP is included in the microinjection mix, another siRNA control specific for GL3 luciferase was used. It is important to note that the GL2 luciferase activity of the HIV LTR reporter used in this study is unaffected by GL3-siRNA. In microinjection experiments Tat transcriptional activity was suppressed 5-fold by p300-siRNA as compared to GL3-siRNA in HeLa cells expressing Tat (FIG. 3C). No difference was observed in Tat-independent LTR activity when the TAR-mutant luciferase construct was injected.

Figure 3D:
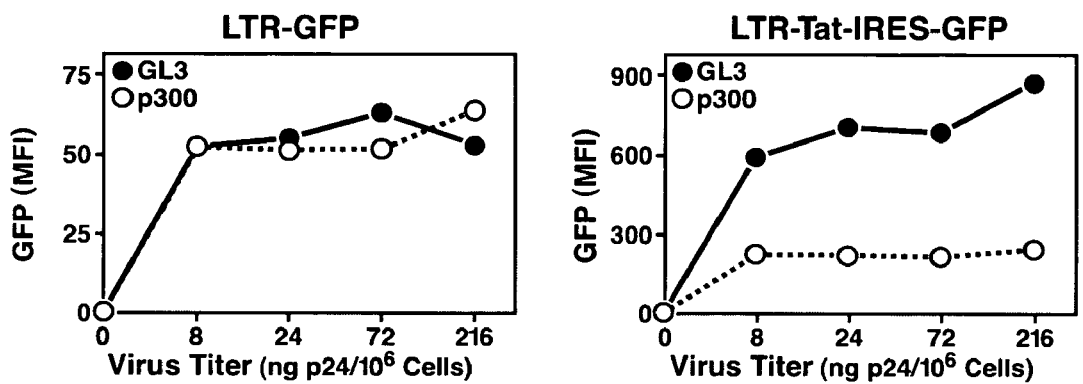

Similar results were obtained in HeLa cells microinjected with the wild-type LTR-luciferase construct and synthetic Tat (FIG. 3C). To further demonstrate the critical role of p300 in Tat-mediated HIV transcription, viral infections with HIV-1-based vectors were performed. HeLa cells transfected with siRNA specific for either p300 or GL3 were infected with Tat-independent (LTR-GFP) or Tat-dependent lentiviral vectors (LTR-Tat-IRES-GFP), pseudotyped with the vesiculo stomatitis virus G protein (VSV-G). Viral expression was monitored by flow cytometric measurement of GFP. Again, Tat-mediated HIV transactivation, expressed as Mean Fluorescence Intensity (MFI), was markedly suppressed, while basal HIV promoter activity was unaffected by the loss of p300 (FIG. 3D). Cells transfected with p300-siRNA and GL3-siRNA were infected by the lentiviral vectors with the same efficiency at each infectious titer (as measured by the percentage of GFP+ cells). This observation rules out that loss of p300 inhibited earlier steps in the viral life cycle before transcription.

AcTat Binds to TAR RNA, CyclinT1 and RNAPII, but Cannot Recruit CyclinT1 to TAR.

The ARM of Tat is a highly conserved region that serves as the TAR RNA binding motif in Tat.

The binding of Tat to the TAR hairpin is mediated by a three-nucleotide U-rich bulge in the TAR stem while the loop sequences are contacted by the Tat cofactor CyclinT1. The interaction of Tat with CyclinT1 is thought to induce a conformational change in Tat that is important for ternary complex formation between Tat, TAR and CyclinT1 (Wei et al., 1998, supra). To determine whether acetylation of the ARM alters binding to TAR RNA, we performed RNA gel mobility assays using the full-length synthetic Tat proteins.

FIGS. 4A-D. (FIG. 4A) Bulge-dependent binding of Tat to TAR. Radiolabeled riboprobes corresponding to the HIV TAR element or a mutated form (TARΔBulge) were incubated with 0, 40, 80 and 160 ng of Tat and analyzed on a 4% Tris-glycine gel. (FIG. 4B) High-affinity binding of AcTat to TAR RNA, but not to CyclinT1. The wild-type TAR probe was incubated with increasing amounts of synthetic Tat or AcTat (0, 1.6 ng, 8 ng, 40 ng, and 200 ng) in the absence or presence of recombinant CyclinT1. The same experiment with a mutated TAR RNA probe containing mutations in the apical loop is shown below (TARΔLoop). (FIG. 4C) Binding of AcTat to CyclinT1 in the absence of TAR. Increasing amounts (0, 0.5 μg, 1 μg, and 2 μg) of Tat or AcTat were incubated with GST-CyclinT1, Tat-binding-deficient GST-CyclinT1 (C261A) or GST alone. Bound proteins were analyzed with monoclonal anti-Tat antibodies, directed against the N-terminus of Tat. 50% of input Tat proteins are shown. (FIG. 4D) Binding of Tat and AcTat to RNAPII. Biotinylated Tat or AcTat proteins (0, 1, 2, 4, 8 μg) were incubated with nuclear extracts, precipitated with streptavidin-sepharose and analyzed with modification-specific antibodies directed against the CTD of RNAPII. AcTat was detected with monoclonal anti-AcARM antibodies. Both Tat proteins reacted with horseradish peroxidase-conjugated streptavidin (SA-HRP).

Figure 4B:
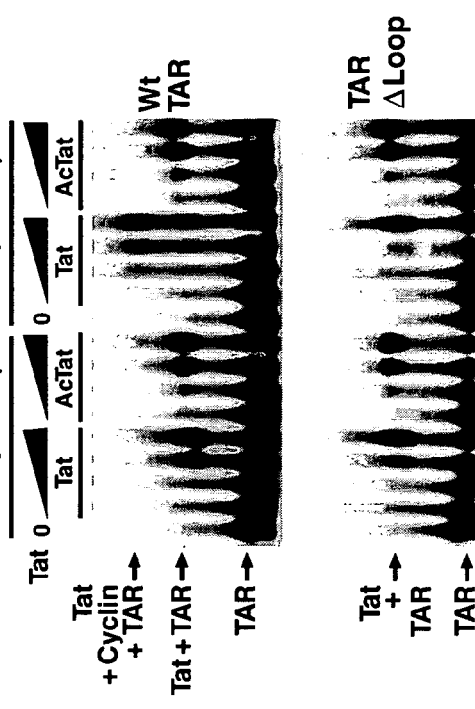
FIGS. 4A-D depict results showing that acetylation of Tat blocks the formation of the ternary Tat/TAR/CyclinT1 complex, but allows binding to RNAPII.
Figure 4A:
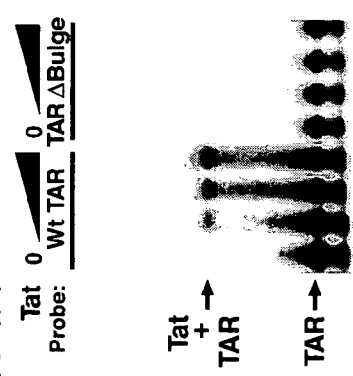

In the absence of CyclinT1, unacetylated Tat associated with wild-type TAR RNA with high affinity (FIG. 4A). Binding was blocked when a bulge-mutant RNA was used as a probe (FIG. 4A). Acetylated Tat bound to TAR with affinities equal to that of unacetylated Tat; in fact, the binding affinity of AcTat appeared slightly enhanced, as formation of retarded bands occurred at one-third the concentration of unacetylated Tat (FIG. 4B). As expected, mutations in the loop of TAR had little effect on the binding of Tat or AcTat (FIG. 4B).

Addition of CyclinT1 to the reaction led to the formation of the ternary complex composed of Tat, TAR and CyclinT1 (FIG. 4B). Remarkably, unacetylated Tat and AcTat reacted differently in the presence of CyclinT1. While unacetylated Tat formed the expected Tat/TAR/CyclinT1 complex, AcTat could not. Addition of CyclinT1 did not alter the affinity of AcTat or unacetylated Tat for wild-type TAR RNA; however, as expected, ternary complex formation of unacetylated Tat with TAR and CyclinT1 was dependent on an intact TAR loop (FIG. 4B). We also incubated the Tat/TAR/CyclinT1 complex with recombinant p300-HAT and acetyl-coenzyme A (AcCoA). Ternary complex formation, but not RNA binding of Tat, was suppressed when binding reactions were incubated in the presence, but not in the absence of AcCoA, confirming these observations.

Figure 4D:
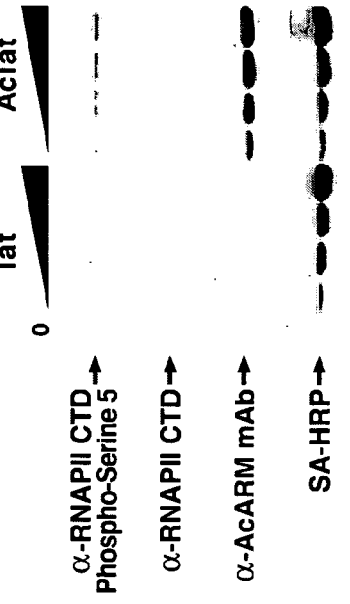
Figure 4C:
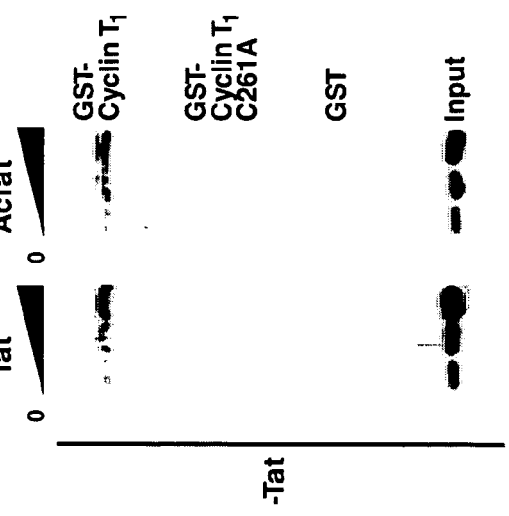

Tat interacts with CyclinT1 through a domain that extends from amino acids 1-48 in Tat. This domain alone is sufficient to bind to CyclinT1 and to compete with full-length Tat to prevent assembly of the Tat/CyclinT1/TAR complex in vitro (Wei et al., 1998, supra). To test whether in the absence of TAR AcTat binds CyclinT1, we performed GST pulldown experiments with synthetic Tat proteins and GST-CyclinT1 (FIG. 4C). Tat and AcTat bound to wild-type GST-CyclinT1 with equal affinities, indicating that the transactivation domain in each synthetic protein was intact. Neither Tat nor AcTat bound to a mutant CyclinT1 in which cysteine at position 261 had been replaced with an alanine or to GST alone, confirming the specific binding conditions.

Evidence has been presented that the formation of the Tat/CyclinT1/CDK9 complex at TAR RNA represents an early step during HIV transcription elongation. During late stages, the Tat protein associates directly with the elongating RNAPII, independently of TAR RNA and CyclinT1. Direct interaction with RNAPII required an intact ARM of Tat and occurred after recruitment of Tat to TAR. Next, we compared the ability of both acetylated and nonacetylated Tat to interact with RNAPII. Biotinylated Tat or AcTat were incubated with nuclear extracts and the bound proteins analyzed by western blotting. This experiment demonstrated that AcTat interacted with the hyperphosphorylated RNAPII complex with higher affinity than Tat (FIG. 4D). In the same experiment, no binding of Tat or AcTat to the nonphosphorylated RNAPII was observed. These data indicate that while AcTat is unable to bind with CyclinT1 to TAR, it shows increased affinity for the elongation-competent RNAPII.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An immunogenic composition comprising an acetylated immunodeficiency virus Tat polypeptide, wherein said polypeptide comprises at least one acetylated lysine residue; and a pharmaceutically acceptable excipient.

2. The immunogenic composition of claim 1, wherein said polypeptide is a human immunodeficiency virus-1 Tat polypeptide, and wherein said acetylated lysine is Lys-50.

3. The immunogenic composition of claim 1, wherein said polypeptide comprises the amino acid sequence as set forth in any one of SEQ ID NOs:1-23.

4. The immunogenic composition of claim 1, wherein said polypeptide comprises the amino acid sequence Ser-Tyr-Gly-Arg-acetylated Lys-Lys-Arg-Arg-Gln-Arg-Cys (SEQ ID NO:03).

5. The immunogenic composition of claim 1, wherein said polypeptide comprises the amino acid sequence Ser-His-Gly-Arg-acetylated Lys-Lys-Arg-Arg-Gln-Arg-Cys (SEQ ID NO:04).

6. The immunogenic composition of claim 1, wherein said polypeptide is linked to a carrier.

7. The immunogenic composition of claim 6, wherein said polypeptide is linked directly to the carrier.

8. The immunogenic composition of claim 6, wherein said polypeptide is linked to said carrier through a linker.

9. The immunogenic composition of claim 6, wherein said carrier is selected from a protein, a polysaccharide, a polyamino acid, an inactivated bacterial toxin, an inactivated bacterium, an inactivated viral particle, a lipid, and a liposome.

10. The immunogenic composition of claim 6, wherein said carrier is selected from tetanus toxoid, diphtheria toxoid, purified protein derivative of *Mycobacterium tuberculosis*, and inactivated exotoxin A from *Pseudomonas aeruginosa*.

11. The immunogenic composition of claim 1, further comprising an adjuvant.

12. The immunogenic composition of claim 11, wherein the adjuvant is an aluminum salt adjuvant.

13. The immunogenic composition of claim 1, further comprising at least a second acetylated immunodeficiency Tat polypeptide.

14. The immunogenic composition of claim 13, wherein said at least second acetylated Tat polypeptide comprises the amino acid sequence set forth in any one of SEQ ID NOs: 1-23.

15. The immunogenic composition of claim 13, wherein said at least second acetylated Tat polypeptide differs from the first acetylated Tat polypeptide amino acid sequence by at least one amino acid.

16. The immunogenic composition of claim 1, further comprising at least a second Tat polypeptide, wherein said at least second Tat polypeptide is not acetylated.

17. The immunogenic composition of claim 16, wherein said at least second Tat polypeptide comprises a sequence of amino acid 1 to amino acid 45 of a Tat polypeptide.

18. The immunogenic composition of claim 16 wherein said at least second Tat polypeptide comprises a sequence of amino acid 55 to amino acid 72 of a Tat polypeptide.

19. The immunogenic composition of claim 16, wherein said at least second Tat polypeptide comprises a sequence of amino acid 1 to amino acid 45 and amino acid 55 to amino acid 72 of a Tat polypeptide.

20. The immunogenic composition of claim 16 wherein said at least second Tat polypeptide comprises the amino acid sequence set forth in any one of SEQ ID NOs: 28-37.

21. The immunogenic composition of claim 1, wherein the acetylated immunodeficiency TAT polypeptide comprises a lipid residue.

22. The immunogenic composition of claim 1, wherein the acetylated Tat polypeptide is multimerized, wherein the multimerized acetylated Tat polypeptide comprises two or more monomeric Tat polypeptides.

23. The immunogenic composition of claim 22, wherein the monomeric Tat polypeptides are linked directly.

24. The immunogenic composition of claim 22, wherein the monomeric Tat polypeptides are linked via a linker.

25. The immunogenic composition of claim 1, wherein the acetylated Tat polypeptide has a length of from 7 amino acids to 72 amino acids.

26. The immunogenic composition of claim 1, wherein the acetylated Tat polypeptide has a length of from 10 amino acids to 25 amino acids.

* * * * *

UNITED STATES PATENT AND TRADEMARK OFFICE
CERTIFICATE OF CORRECTION

PATENT NO. : 7,482,016 B2  Page 1 of 1
APPLICATION NO. : 10/799854
DATED : January 27, 2009
INVENTOR(S) : Alexander P. Dörr et al.

It is certified that error appears in the above-identified patent and that said Letters Patent is hereby corrected as shown below:

Please replace the Statement Regarding Federally Sponsored Research beginning on column 1, line 15, with the following revised statement:

STATEMENT REGARDING FEDERALLY SPONSORED RESEARCH

--The U.S. government has certain rights in this invention, pursuant to grant no. AI40847 awarded by the National Institutes of Health.--

Signed and Sealed this

First Day of December, 2009

David J. Kappos
*Director of the United States Patent and Trademark Office*

SEQUENCE LISTING

```
<160> NUMBER OF SEQ ID NOS: 65

<210> SEQ ID NO 1
<211> LENGTH: 19
<212> TYPE: PRT
<213> ORGANISM: Artificial Sequence
<220> FEATURE:
<223> OTHER INFORMATION: synthetic protein
<220> FEATURE:
<221> NAME/KEY: VARIANT
<222> LOCATION: (2)...(2)
<223> OTHER INFORMATION: Xaa = Ala or Gly
<220> FEATURE:
<221> NAME/KEY: VARIANT
<222> LOCATION: (13)...(13)
<223> OTHER INFORMATION: Xaa = Arg or Lys
<220> FEATURE:
<221> NAME/KEY: VARIANT
<222> LOCATION: (14)...(14)
<223> OTHER INFORMATION: Xaa = Gln or His
<220> FEATURE:
<221> NAME/KEY: VARIANT
<222> LOCATION: (17)...(17)
<223> OTHER INFORMATION: Xaa = Arg or Gly or Lys or Ser
<220> FEATURE:
```

```
<221> NAME/KEY: VARIANT
<222> LOCATION: (18)...(18)
<223> OTHER INFORMATION: Xaa = Pro or Ala or Thr
<220> FEATURE:
<221> NAME/KEY: VARIANT
<222> LOCATION: (19)...(19)
<223> OTHER INFORMATION: Xaa = Gln or Pro or Thr

<400> SEQUENCE: 1

Lys Xaa Leu Gly Ile Ser Tyr Gly Arg Lys Lys Arg Xaa Xaa Arg Arg
 1               5                  10                  15

Xaa Xaa Xaa

<210> SEQ ID NO 2
<211> LENGTH: 11
<212> TYPE: PRT
<213> ORGANISM: Artificial Sequence
<220> FEATURE:
<223> OTHER INFORMATION: synthetic protein
<220> FEATURE:
<221> NAME/KEY: ACETYLATION
<222> LOCATION: (5)...(5)
<223> OTHER INFORMATION: Xaa = Acetylated lysine

<400> SEQUENCE: 2

Ser Tyr Gly Arg Xaa Lys Lys Arg Arg Gln Arg
 1               5                  10

<210> SEQ ID NO 3
<211> LENGTH: 11
<212> TYPE: PRT
<213> ORGANISM: Artificial Sequence
<220> FEATURE:
<223> OTHER INFORMATION: synthetic protein
<220> FEATURE:
<221> NAME/KEY: ACETYLATION
<222> LOCATION: (5)...(5)
<223> OTHER INFORMATION: Xaa = Acetylated lysine

<400> SEQUENCE: 3

Ser Tyr Gly Arg Xaa Lys Arg Arg Gln Arg Cys
 1               5                  10

<210> SEQ ID NO 4
<211> LENGTH: 11
<212> TYPE: PRT
<213> ORGANISM: Artificial Sequence
<220> FEATURE:
<223> OTHER INFORMATION: synthetic protein
<220> FEATURE:
<221> NAME/KEY: ACETYLATION
<222> LOCATION: (5)...(5)
<223> OTHER INFORMATION: Xaa = Acetylated lysine

<400> SEQUENCE: 4

Ser His Gly Arg Xaa Lys Arg Arg Gln Arg Cys
 1               5                  10

<210> SEQ ID NO 5
<211> LENGTH: 20
<212> TYPE: PRT
<213> ORGANISM: Artificial Sequence
<220> FEATURE:
<223> OTHER INFORMATION: synthetic protein
<220> FEATURE:
<221> NAME/KEY: ACETYLATION
<222> LOCATION: (10)...(10)
<223> OTHER INFORMATION: Xaa = Acetylated lysine

<400> SEQUENCE: 5
```

Lys Gly Leu Gly Ile Ser Tyr Gly Arg Xaa Lys Arg Arg Gln Arg Arg
1               5                   10                  15

Arg Thr Pro Gln
            20

<210> SEQ ID NO 6
<211> LENGTH: 20
<212> TYPE: PRT
<213> ORGANISM: Artificial Sequence
<220> FEATURE:
<223> OTHER INFORMATION: synthetic protein
<220> FEATURE:
<221> NAME/KEY: ACETYLATION
<222> LOCATION: (10)...(10)
<223> OTHER INFORMATION: Xaa = Acetylated lysine

<400> SEQUENCE: 6

Lys Ala Leu Gly Ile Ser Tyr Gly Arg Xaa Lys Arg Arg Gln Arg Arg
1               5                   10                  15

Arg Thr Ser Gln
            20

<210> SEQ ID NO 7
<211> LENGTH: 20
<212> TYPE: PRT
<213> ORGANISM: Artificial Sequence
<220> FEATURE:
<223> OTHER INFORMATION: synthetic protein
<220> FEATURE:
<221> NAME/KEY: ACETYLATION
<222> LOCATION: (10)...(10)
<223> OTHER INFORMATION: Xaa = Acetylated lysine

<400> SEQUENCE: 7

Lys Ala Leu Gly Ile Ser Tyr Gly Arg Xaa Lys Arg Arg Gln Arg Arg
1               5                   10                  15

Arg Thr Ala Gln
            20

<210> SEQ ID NO 8
<211> LENGTH: 20
<212> TYPE: PRT
<213> ORGANISM: Artificial Sequence
<220> FEATURE:
<223> OTHER INFORMATION: synthetic protein
<220> FEATURE:
<221> NAME/KEY: ACETYLATION
<222> LOCATION: (10)...(10)
<223> OTHER INFORMATION: Xaa = Acetylated lysine

<400> SEQUENCE: 8

Lys Gly Leu Gly Ile Ser His Gly Arg Xaa Lys Arg Arg Gln Arg Arg
1               5                   10                  15

Arg Thr Pro Pro
            20

<210> SEQ ID NO 9
<211> LENGTH: 20
<212> TYPE: PRT
<213> ORGANISM: Artificial Sequence
<220> FEATURE:
<223> OTHER INFORMATION: synthetic protein
<220> FEATURE:
<221> NAME/KEY: ACETYLATION
<222> LOCATION: (10)...(10)
<223> OTHER INFORMATION: Xaa = Acetylated lysine -continued

```
<400> SEQUENCE: 9

Lys Gly Leu Gly Ile Ser Tyr Gly Arg Xaa Lys Arg Arg Gln Arg Arg
 1               5                  10                  15

Arg Ala Ala Gln
            20

<210> SEQ ID NO 10
<211> LENGTH: 20
<212> TYPE: PRT
<213> ORGANISM: Artificial Sequence
<220> FEATURE:
<223> OTHER INFORMATION: synthetic protein
<220> FEATURE:
<221> NAME/KEY: ACETYLATION
<222> LOCATION: (10)...(10)
<223> OTHER INFORMATION: Xaa = Acetylated lysine

<400> SEQUENCE: 10

Lys Gly Leu Gly Ile Ser Tyr Gly Arg Xaa Lys Arg Arg Gln Arg Arg
 1               5                  10                  15

Arg Ala Pro Gln
            20

<210> SEQ ID NO 11
<211> LENGTH: 20
<212> TYPE: PRT
<213> ORGANISM: Artificial Sequence
<220> FEATURE:
<223> OTHER INFORMATION: synthetic protein
<220> FEATURE:
<221> NAME/KEY: ACETYLATION
<222> LOCATION: (10)...(10)
<223> OTHER INFORMATION: Xaa = acetylated lysine

<400> SEQUENCE: 11

Lys Gly Leu Gly Ile Ser Tyr Gly Arg Xaa Lys Arg Arg Gln Arg Arg
 1               5                  10                  15

Arg Ser Pro Gln
            20

<210> SEQ ID NO 12
<211> LENGTH: 20
<212> TYPE: PRT
<213> ORGANISM: Artificial Sequence
<220> FEATURE:
<223> OTHER INFORMATION: synthetic protein
<220> FEATURE:
<221> NAME/KEY: ACETYLATION
<222> LOCATION: (10)...(10)
<223> OTHER INFORMATION: Xaa = acetylated lysine

<400> SEQUENCE: 12

Lys Gly Leu Gly Ile Ser Tyr Gly Arg Xaa Lys Arg Arg Gln Arg Arg
 1               5                  10                  15

Arg Pro Pro Gln
            20

<210> SEQ ID NO 13
<211> LENGTH: 20
<212> TYPE: PRT
<213> ORGANISM: Artificial Sequence
<220> FEATURE:
<223> OTHER INFORMATION: synthetic protein
<220> FEATURE:
<221> NAME/KEY: ACETYLATION
<222> LOCATION: (10)...(10)
<223> OTHER INFORMATION: Xaa = Acetylated lysine
```

```
<400> SEQUENCE: 13

Lys Gly Leu Gly Ile Ser Tyr Gly Arg Xaa Lys Arg Arg Gln Arg
1               5                   10                  15

Arg Thr His Gln
            20

<210> SEQ ID NO 14
<211> LENGTH: 18
<212> TYPE: PRT
<213> ORGANISM: Artificial Sequence
<220> FEATURE:
<223> OTHER INFORMATION: synthetic protein
<220> FEATURE:
<221> NAME/KEY: ACETYLATION
<222> LOCATION: (9)...(9)
<223> OTHER INFORMATION: Xaa = acetylated lysine

<400> SEQUENCE: 14

Gly Leu Gly Ile Ser Tyr Gly Arg Xaa Lys Arg Arg Gln Arg Arg
1               5                   10                  15

Thr Pro

<210> SEQ ID NO 15
<211> LENGTH: 18
<212> TYPE: PRT
<213> ORGANISM: Artificial Sequence
<220> FEATURE:
<223> OTHER INFORMATION: synthetic protein
<220> FEATURE:
<221> NAME/KEY: ACETYLATION
<222> LOCATION: (9)...(9)
<223> OTHER INFORMATION: Xaa = acetylated lysine

<400> SEQUENCE: 15

Ala Leu Gly Ile Ser Tyr Gly Arg Xaa Lys Arg Arg Gln Arg Arg
1               5                   10                  15

Thr Ser

<210> SEQ ID NO 16
<211> LENGTH: 18
<212> TYPE: PRT
<213> ORGANISM: Artificial Sequence
<220> FEATURE:
<223> OTHER INFORMATION: synthetic protein
<220> FEATURE:
<221> NAME/KEY: ACETYLATION
<222> LOCATION: (9)...(9)
<223> OTHER INFORMATION: Xaa = acetylated lysine

<400> SEQUENCE: 16

Ala Leu Gly Ile Ser Tyr Gly Arg Xaa Lys Arg Arg Gln Arg Arg
1               5                   10                  15

Thr Ala

<210> SEQ ID NO 17
<211> LENGTH: 18
<212> TYPE: PRT
<213> ORGANISM: Artificial Sequence
<220> FEATURE:
<223> OTHER INFORMATION: synthetic protein
<220> FEATURE:
<221> NAME/KEY: ACETYLATION
<222> LOCATION: (9)...(9)
<223> OTHER INFORMATION: Xaa = acetylated lysine

<400> SEQUENCE: 17
```

```
Gly Leu Gly Ile Ser His Gly Arg Xaa Lys Arg Arg Gln Arg Arg
1               5                   10                  15

Thr Pro

<210> SEQ ID NO 18
<211> LENGTH: 18
<212> TYPE: PRT
<213> ORGANISM: Artificial Sequence
<220> FEATURE:
<223> OTHER INFORMATION: synthetic protein
<220> FEATURE:
<221> NAME/KEY: ACETYLATION
<222> LOCATION: (9)...(9)
<223> OTHER INFORMATION: Xaa = acetylated lysine

<400> SEQUENCE: 18

Gly Leu Gly Ile Ser Tyr Gly Arg Xaa Lys Arg Arg Gln Arg Arg
1               5                   10                  15

Ala Ala

<210> SEQ ID NO 19
<211> LENGTH: 18
<212> TYPE: PRT
<213> ORGANISM: Artificial Sequence
<220> FEATURE:
<223> OTHER INFORMATION: synthetic protein
<220> FEATURE:
<221> NAME/KEY: ACETYLATION
<222> LOCATION: (9)...(9)
<223> OTHER INFORMATION: Xaa = acetylated lycine

<400> SEQUENCE: 19

Gly Leu Gly Ile Ser Tyr Gly Arg Xaa Lys Arg Arg Gln Arg Arg
1               5                   10                  15

Ala Pro

<210> SEQ ID NO 20
<211> LENGTH: 18
<212> TYPE: PRT
<213> ORGANISM: Artificial Sequence
<220> FEATURE:
<223> OTHER INFORMATION: synthetic protein
<220> FEATURE:
<221> NAME/KEY: ACETYLATION
<222> LOCATION: (9)...(9)
<223> OTHER INFORMATION: Xaa = acetylated lycine

<400> SEQUENCE: 20

Gly Leu Gly Ile Ser Tyr Gly Arg Xaa Lys Arg Arg Gln Arg Arg
1               5                   10                  15

Ser Pro

<210> SEQ ID NO 21
<211> LENGTH: 18
<212> TYPE: PRT
<213> ORGANISM: Artificial Sequence
<220> FEATURE:
<223> OTHER INFORMATION: synthetic protein
<220> FEATURE:
<221> NAME/KEY: ACETYLATION
<222> LOCATION: (9)...(9)
<223> OTHER INFORMATION: Xaa = acetylated lycine

<400> SEQUENCE: 21

Gly Leu Gly Ile Ser Tyr Gly Arg Xaa Lys Arg Arg Gln Arg Arg
1               5                   10                  15
```

Pro Pro

```
<210> SEQ ID NO 22
<211> LENGTH: 18
<212> TYPE: PRT
<213> ORGANISM: Artificial Sequence
<220> FEATURE:
<223> OTHER INFORMATION: synthetic protein
<220> FEATURE:
<221> NAME/KEY: ACETYLATION
<222> LOCATION: (9)...(9)
<223> OTHER INFORMATION: Xaa = acetylated lycine

<400> SEQUENCE: 22

Gly Leu Gly Ile Ser Tyr Gly Arg Xaa Lys Arg Arg Gln Arg Arg
 1               5                  10                  15

Thr His

<210> SEQ ID NO 23
<211> LENGTH: 20
<212> TYPE: PRT
<213> ORGANISM: Artificial Sequence
<220> FEATURE:
<223> OTHER INFORMATION: synthetic protein
<220> FEATURE:
<221> NAME/KEY: ACETYLATION
<222> LOCATION: (10)...(10)
<223> OTHER INFORMATION: Xaa = acetylated lycine

<400> SEQUENCE: 23

Lys Gly Leu Gly Ile Ser Tyr Gly Arg Xaa Lys Arg Arg His Arg Arg
 1               5                  10                  15

Arg Thr Pro Gln
            20

<210> SEQ ID NO 24
<211> LENGTH: 6
<212> TYPE: PRT
<213> ORGANISM: Artificial Sequence
<220> FEATURE:
<223> OTHER INFORMATION: synthetic protein

<400> SEQUENCE: 24

Ala Ala Ala Gly Gly Met
 1               5

<210> SEQ ID NO 25
<211> LENGTH: 14
<212> TYPE: PRT
<213> ORGANISM: Artificial Sequence
<220> FEATURE:
<223> OTHER INFORMATION: synthetic protein

<400> SEQUENCE: 25

Ala Ala Ala Gly Gly Met Pro Pro Ala Ala Ala Gly Gly Met
 1               5                  10

<210> SEQ ID NO 26
<211> LENGTH: 6
<212> TYPE: PRT
<213> ORGANISM: Artificial Sequence
<220> FEATURE:
<223> OTHER INFORMATION: synthetic protein

<400> SEQUENCE: 26

Ala Ala Ala Gly Gly Met
```

```
1               5

<210> SEQ ID NO 27
<211> LENGTH: 8
<212> TYPE: PRT
<213> ORGANISM: Artificial Sequence
<220> FEATURE:
<223> OTHER INFORMATION: synthetic protein

<400> SEQUENCE: 27

Pro Pro Ala Ala Ala Gly Gly Met
1               5

<210> SEQ ID NO 28
<211> LENGTH: 10
<212> TYPE: PRT
<213> ORGANISM: Artificial Sequence
<220> FEATURE:
<223> OTHER INFORMATION: synthetic protein

<400> SEQUENCE: 28

Met Glu Pro Val Asp Pro Ser Leu Glu Pro
1               5                   10

<210> SEQ ID NO 29
<211> LENGTH: 15
<212> TYPE: PRT
<213> ORGANISM: Artificial Sequence
<220> FEATURE:
<223> OTHER INFORMATION: synthetic protein

<400> SEQUENCE: 29

Met Glu Pro Val Asp Pro Ser Leu Glu Pro Trp Lys His Pro Gly
1               5                   10                  15

<210> SEQ ID NO 30
<211> LENGTH: 20
<212> TYPE: PRT
<213> ORGANISM: Artificial Sequence
<220> FEATURE:
<223> OTHER INFORMATION: synthetic protein

<400> SEQUENCE: 30

Met Glu Pro Val Asp Pro Ser Leu Glu Pro Trp Lys His Pro Gly Ser
1               5                   10                  15

Gln Pro Lys Thr
            20

<210> SEQ ID NO 31
<211> LENGTH: 15
<212> TYPE: PRT
<213> ORGANISM: Artificial Sequence
<220> FEATURE:
<223> OTHER INFORMATION: synthetic protein

<400> SEQUENCE: 31

Pro Ser Leu Glu Pro Trp Lys His Pro Gly Ser Gln Pro Lys Thr
1               5                   10                  15

<210> SEQ ID NO 32
<211> LENGTH: 20
<212> TYPE: PRT
<213> ORGANISM: Artificial Sequence
<220> FEATURE:
<223> OTHER INFORMATION: synthetic protein

<400> SEQUENCE: 32
```

Pro Ser Leu Glu Pro Trp Lys His Pro Gly Ser Gln Pro Lys Thr Ala
1               5                   10                  15

Cys Asn Asn Cys
            20

<210> SEQ ID NO 33
<211> LENGTH: 20
<212> TYPE: PRT
<213> ORGANISM: Artificial Sequence
<220> FEATURE:
<223> OTHER INFORMATION: synthetic protein

<400> SEQUENCE: 33

Trp Lys His Pro Gly Ser Gln Pro Lys Thr Ala Cys Asn Asn Cys Tyr
1               5                   10                  15

Cys Lys Arg Cys
            20

<210> SEQ ID NO 34
<211> LENGTH: 15
<212> TYPE: PRT
<213> ORGANISM: Artificial Sequence
<220> FEATURE:
<223> OTHER INFORMATION: synthetic protein

<400> SEQUENCE: 34

Ser Gln Pro Lys Thr Ala Cys Asn Asn Cys Tyr Cys Lys Arg Cys
1               5                   10                  15

<210> SEQ ID NO 35
<211> LENGTH: 20
<212> TYPE: PRT
<213> ORGANISM: Artificial Sequence
<220> FEATURE:
<223> OTHER INFORMATION: synthetic protein

<400> SEQUENCE: 35

Ser Gln Pro Lys Thr Ala Cys Asn Asn Cys Tyr Cys Lys Arg Cys Cys
1               5                   10                  15

Phe His Cys Gln
            20

<210> SEQ ID NO 36
<211> LENGTH: 20
<212> TYPE: PRT
<213> ORGANISM: Artificial Sequence
<220> FEATURE:
<223> OTHER INFORMATION: synthetic protein

<400> SEQUENCE: 36

Ala Cys Asn Asn Cys Tyr Cys Lys Arg Cys Cys Phe His Cys Gln Val
1               5                   10                  15

Cys Phe Ile Lys
            20

<210> SEQ ID NO 37
<211> LENGTH: 20
<212> TYPE: PRT
<213> ORGANISM: Artificial Sequence
<220> FEATURE:
<223> OTHER INFORMATION: synthetic protein

<400> SEQUENCE: 37

Tyr Cys Lys Arg Cys Cys Phe His Cys Gln Val Cys Phe Ile Lys Lys

```
                1               5                  10                 15
Gly Leu Gly Ile
            20

<210> SEQ ID NO 38
<211> LENGTH: 22
<212> TYPE: DNA
<213> ORGANISM: Artificial Sequence
<220> FEATURE:
<223> OTHER INFORMATION: primer

<400> SEQUENCE: 38
ttgcctgtac tgggtctctc tg                                               22

<210> SEQ ID NO 39
<211> LENGTH: 21
<212> TYPE: DNA
<213> ORGANISM: Artificial Sequence
<220> FEATURE:
<223> OTHER INFORMATION: primer

<400> SEQUENCE: 39
tcgctttcag gtccctgttc g                                                21

<210> SEQ ID NO 40
<211> LENGTH: 24
<212> TYPE: DNA
<213> ORGANISM: Artificial Sequence
<220> FEATURE:
<223> OTHER INFORMATION: primer

<400> SEQUENCE: 40
tgcatagaag gacccagata ggtc                                             24

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
tcaatgaccc tgagcccaag                                                  20

<210> SEQ ID NO 42
<211> LENGTH: 101
<212> TYPE: PRT
<213> ORGANISM: human immunodeficiency virus

<400> SEQUENCE: 42

Met Glu Pro Val Asp Pro Arg Leu Glu Pro Trp Lys His Pro Gly Ser
 1               5                  10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu Ser Lys Lys Val Glu Arg Glu Thr Glu
                85                  90                  95
```

-continued

```
Thr Asp Pro Phe Asp
            100

<210> SEQ ID NO 43
<211> LENGTH: 86
<212> TYPE: PRT
<213> ORGANISM: human immunodeficiency virus

<400> SEQUENCE: 43

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu
            85

<210> SEQ ID NO 44
<211> LENGTH: 86
<212> TYPE: PRT
<213> ORGANISM: human immunodeficiency virus

<400> SEQUENCE: 44

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Ala Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu
            85

<210> SEQ ID NO 45
<211> LENGTH: 86
<212> TYPE: PRT
<213> ORGANISM: human immunodeficiency virus

<400> SEQUENCE: 45

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Pro Thr Ser Gln Pro Arg Gly Asp
65                  70                  75                  80

Pro Thr Gly Pro Lys Glu
```

<210> SEQ ID NO 46
<211> LENGTH: 86
<212> TYPE: PRT
<213> ORGANISM: human immunodeficiency virus

<400> SEQUENCE: 46

Met Glu Pro Val Asp Pro Arg Leu Glu Pro Trp Lys His Pro Gly Ser
1               5                   10                  15

Gln Pro Lys Thr Ala Cys Thr Thr Cys Tyr Cys Lys Lys Cys Cys Phe
            20                  25                  30

His Cys Gln Val Cys Phe Thr Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Pro Thr Ser Gln Pro Arg Gly Asp
65                  70                  75                  80

Pro Thr Gly Pro Lys Glu
                85

<210> SEQ ID NO 47
<211> LENGTH: 101
<212> TYPE: PRT
<213> ORGANISM: human immunodeficiency virus

<400> SEQUENCE: 47

Met Glu Pro Val Asp Pro Arg Leu Glu Pro Trp Lys His Pro Gly Ser
1               5                   10                  15

Gln Pro Lys Thr Ala Cys Asn Asn Cys Tyr Cys Lys Lys Cys Cys Tyr
            20                  25                  30

His Cys Gln Val Cys Phe Leu Thr Lys Gly Leu Gly Ile Ser Tyr Gly
        35                  40                  45

Arg Lys Lys Arg Arg Gln Arg Arg Gly Pro Pro Gln Gly Ser Gln Thr
    50                  55                  60

His Gln Val Ser Leu Ser Lys Gln Pro Thr Ser Gln Pro Arg Gly Asp
65                  70                  75                  80

Pro Thr Pro Lys Glu Ser Lys Glu Lys Val Glu Arg Glu Thr Glu Thr
                85                  90                  95

Asp Pro Ala Val Gln
            100

<210> SEQ ID NO 48
<211> LENGTH: 86
<212> TYPE: PRT
<213> ORGANISM: human immunodeficiency virus

<400> SEQUENCE: 48

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Ala His Gln Asn Ser Gln Thr
    50                  55                  60

His Gln Ala Ser Leu Ser Lys Gln Pro Thr Ser Gln Pro Arg Gly Asp
65                  70                  75                  80

Pro Thr Gly Pro Lys Glu
            85

<210> SEQ ID NO 49
<211> LENGTH: 101
<212> TYPE: PRT
<213> ORGANISM: human immunodeficiency virus

<400> SEQUENCE: 49

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Thr Lys Lys Ala Leu Gly Ile Ser Tyr Gly
        35                  40                  45

Arg Lys Lys Arg Arg Gln Arg Arg Ala His Gln Asp Ser Gln Asn
    50                  55                  60

His Gln Ala Ser Leu Ser Lys Gln Pro Ser Ser Gln Thr Arg Gly Asp
65                  70                  75                  80

Pro Thr Gly Pro Lys Glu Pro Lys Lys Glu Val Glu Arg Glu Ala Glu
                85                  90                  95

Thr Asp Pro Leu Asp
            100

<210> SEQ ID NO 50
<211> LENGTH: 101
<212> TYPE: PRT
<213> ORGANISM: human immunodeficiency virus

<400> SEQUENCE: 50

Met Glu Pro Val Asp Pro Asn Leu Glu Pro Trp Lys His Pro Gly Ser
1               5                   10                  15

Gln Pro Arg Thr Ala Cys Thr Asn Cys Tyr Cys Lys Lys Cys Cys Phe
            20                  25                  30

His Cys Gln Val Cys Phe Ile Thr Lys Gly Leu Gly Ile Ser Tyr Gly
        35                  40                  45

Arg Lys Lys Arg Arg Gln Arg Gln Arg Ala Pro Asp Ser Ser Gln Asn
    50                  55                  60

His Gln Asp Ser Leu Ser Lys Gln Pro Ser Ser Gln Pro Arg Gly Asp
65                  70                  75                  80

Pro Thr Gly Pro Lys Glu Ser Lys Lys Glu Val Glu Arg Glu Thr Glu
                85                  90                  95

Thr Asp Pro Leu Asp
            100

<210> SEQ ID NO 51
<211> LENGTH: 86
<212> TYPE: PRT
<213> ORGANISM: human immunodeficiency virus

<400> SEQUENCE: 51

Met Asp Pro Val Asp Pro Asn Leu Glu Pro Trp Asn His Pro Gly Ser
1               5                   10                  15

Gln Pro Lys Thr Ala Cys Asn Arg Cys His Cys Lys Lys Cys Cys Tyr
            20                  25                  30

His Cys Gln Val Cys Phe Ile Thr Lys Gly Leu Gly Ile Ser Tyr Gly
        35                  40                  45

-continued

Arg Lys Lys Arg Arg Gln Arg Arg Pro Ser Gln Gly Gly Gln Thr
    50                  55                  60

His Gln Asp Pro Ile Pro Lys Gln Pro Ser Ser Gln Pro Arg Gly Asn
 65                  70                  75                  80

Pro Thr Gly Pro Lys Glu
                 85

<210> SEQ ID NO 52
<211> LENGTH: 86
<212> TYPE: PRT
<213> ORGANISM: human immunodeficiency virus

<400> SEQUENCE: 52

Met Asp Pro Val Asp Pro Asn Ile Glu Pro Trp Asn His Pro Gly Ser
  1               5                  10                  15

Gln Pro Lys Thr Ala Cys Asn Arg Cys His Cys Lys Lys Cys Cys Tyr
                 20                  25                  30

His Cys Gln Val Cys Phe Ile Thr Lys Gly Leu Gly Ile Ser Tyr Gly
             35                  40                  45

Arg Lys Lys Arg Arg Gln Arg Arg Pro Ser Gln Gly Gly Gln Thr
    50                  55                  60

His Gln Asp Pro Ile Pro Lys Gln Pro Ser Ser Gln Pro Arg Gly Asp
 65                  70                  75                  80

Pro Thr Gly Pro Lys Glu
                 85

<210> SEQ ID NO 53
<211> LENGTH: 99
<212> TYPE: PRT
<213> ORGANISM: human immunodeficiency virus

<400> SEQUENCE: 53

Met Asp Pro Val Asp Pro Asn Leu Glu Pro Trp Asn His Pro Gly Ser
  1               5                  10                  15

Gln Pro Arg Thr Pro Cys Asn Lys Cys His Cys Lys Lys Cys Cys Tyr
                 20                  25                  30

His Cys Pro Val Cys Phe Leu Asn Lys Gly Leu Gly Ile Ser Tyr Gly
             35                  40                  45

Arg Lys Lys Arg Arg Gln Arg Arg Gly Pro Pro Gln Gly Gly Gln Ala
    50                  55                  60

His Gln Val Pro Ile Pro Lys Gln Pro Ser Ser Gln Pro Arg Gly Asp
 65                  70                  75                  80

Pro Thr Gly Pro Lys Glu Gln Lys Lys Lys Val Glu Ser Glu Ala Glu
                 85                  90                  95

Thr Asp Pro

<210> SEQ ID NO 54
<211> LENGTH: 86
<212> TYPE: PRT
<213> ORGANISM: human immunodeficiency virus

<400> SEQUENCE: 54

Met Asp Pro Val Asp Pro Asn Leu Glu Ser Trp Asn His Pro Gly Ser
  1               5                  10                  15

Gln Pro Arg Thr Ala Cys Asn Lys Cys His Cys Lys Lys Cys Cys Tyr
                 20                  25                  30

His Cys Gln Val Cys Phe Ile Thr Lys Gly Leu Gly Ile Ser Tyr Gly
             35                  40                  45

-continued

```
Arg Lys Lys Arg Arg Gln Arg Lys Pro Pro Gln Gly Asp Gln Ala
     50                  55                  60
His Gln Val Pro Ile Pro Glu Gln Pro Ser Ser Gln Ser Arg Gly Asp
 65                  70                  75                  80
Pro Thr Gly Pro Lys Lys
                 85

<210> SEQ ID NO 55
<211> LENGTH: 87
<212> TYPE: PRT
<213> ORGANISM: human immunodeficiency virus

<400> SEQUENCE: 55

Met Asp Pro Val Asp Pro Asn Leu Glu Pro Trp Asn His Pro Gly Ser
  1               5                  10                  15
Gln Pro Arg Thr Pro Cys Asn Lys Cys Tyr Cys Lys Lys Cys Cys Tyr
                 20                  25                  30
His Cys Gln Met Cys Phe Ile Thr Lys Gly Leu Gly Ile Ser Tyr Gly
             35                  40                  45
Arg Lys Lys Arg Arg Gln Arg Arg Pro Pro Gln Gly Asn Gln Ala
     50                  55                  60
His Gln Asp Pro Leu Pro Glu Gln Pro Ser Ser Gln His Arg Gly Asp
 65                  70                  75                  80
His Pro Thr Gly Pro Lys Glu
                 85

<210> SEQ ID NO 56
<211> LENGTH: 101
<212> TYPE: PRT
<213> ORGANISM: human immunodeficiency virus

<400> SEQUENCE: 56

Met Glu Pro Val Asp Pro Asn Leu Glu Pro Trp Lys His Pro Gly Ser
  1               5                  10                  15
Gln Pro Thr Thr Ala Cys Ser Asn Cys Tyr Cys Lys Val Cys Cys Trp
                 20                  25                  30
His Cys Gln Leu Cys Phe Leu Lys Lys Gly Leu Gly Ile Ser Tyr Gly
             35                  40                  45
Lys Lys Lys Arg Lys Pro Arg Arg Gly Pro Pro Gln Gly Ser Lys Asp
     50                  55                  60
His Gln Thr Leu Ile Pro Lys Gln Pro Leu Pro Gln Ser Gln Arg Val
 65                  70                  75                  80
Ser Ala Gly Gln Glu Glu Ser Lys Lys Lys Val Glu Ser Lys Ala Lys
                 85                  90                  95
Thr Asp Arg Phe Ala
            100

<210> SEQ ID NO 57
<211> LENGTH: 101
<212> TYPE: PRT
<213> ORGANISM: human immunodeficiency virus

<400> SEQUENCE: 57

Met Glu Pro Val Asp Pro Asn Leu Glu Pro Trp Lys His Pro Gly Ser
  1               5                  10                  15
Gln Pro Arg Thr Ala Cys Asn Asn Cys Tyr Cys Lys Lys Cys Cys Phe
                 20                  25                  30
```

His Cys Tyr Ala Cys Phe Thr Arg Lys Gly Leu Gly Ile Ser Tyr Gly
            35                  40                  45

Arg Lys Lys Arg Arg Gln Arg Arg Ala Pro Gln Asp Ser Gln Thr
 50                  55                  60

His Gln Ala Ser Leu Ser Lys Gln Pro Ala Ser Gln Ser Arg Gly Asp
 65                  70                  75                  80

Pro Thr Gly Pro Thr Glu Ser Lys Lys Lys Val Glu Arg Glu Thr Glu
                85                  90                  95

Thr Asp Pro Phe Asp
            100

<210> SEQ ID NO 58
<211> LENGTH: 101
<212> TYPE: PRT
<213> ORGANISM: human immunodeficiency virus

<400> SEQUENCE: 58

Met Glu Pro Val Asp Pro Asn Leu Glu Pro Trp Lys His Pro Gly Ser
  1               5                  10                  15

Gln Pro Arg Thr Ala Cys Asn Asn Cys Tyr Cys Lys Lys Cys Cys Phe
                20                  25                  30

His Cys Gln Val Cys Phe Thr Lys Lys Gly Leu Gly Ile Ser Tyr Gly
            35                  40                  45

Arg Lys Lys Arg Arg Gln Arg Arg Pro Pro Gln Asp Ser Gln Thr
 50                  55                  60

His Gln Ser Ser Leu Ser Lys Gln Pro Thr Ser Gln Leu Arg Gly Asp
 65                  70                  75                  80

Pro Thr Gly Pro Thr Glu Ser Lys Lys Lys Val Glu Arg Glu Thr Glu
                85                  90                  95

Thr Asp Pro Val His
            100

<210> SEQ ID NO 59
<211> LENGTH: 101
<212> TYPE: PRT
<213> ORGANISM: human immunodeficiency virus

<400> SEQUENCE: 59

Met Glu Pro Val Asp Pro Arg Leu Glu Pro Trp Lys His Pro Gly Ser
  1               5                  10                  15

Gln Pro Lys Thr Ala Ser Asn Asn Cys Tyr Cys Lys Arg Cys Cys Leu
                20                  25                  30

His Cys Gln Val Cys Phe Thr Lys Lys Gly Leu Gly Ile Ser Tyr Gly
            35                  40                  45

Arg Lys Lys Arg Arg Gln Arg Arg Ala Pro Gln Asp Ser Lys Thr
 50                  55                  60

His Val Ser Leu Ser Lys Gln Pro Ala Ser Gln Pro Arg Gly Asp
 65                  70                  75                  80

Pro Thr Gly Pro Lys Glu Ser Lys Lys Lys Val Glu Arg Glu Thr Glu
                85                  90                  95

Thr Asp Pro Glu Asp
            100

<210> SEQ ID NO 60
<211> LENGTH: 58
<212> TYPE: PRT
<213> ORGANISM: human immunodeficiency virus

```
<400> SEQUENCE: 60

Met Glu Pro Val Asp Pro Arg Leu Glu Pro Trp Lys His Pro Gly Ser
 1               5                  10                  15

Gln Pro Lys Thr Ala Cys Thr Thr Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Ala
    50                  55

<210> SEQ ID NO 61
<211> LENGTH: 101
<212> TYPE: PRT
<213> ORGANISM: human immunodeficiency virus

<400> SEQUENCE: 61

Met Glu Pro Val Asp Pro Arg Leu Glu Pro Trp Lys His Pro Gly Ser
 1               5                  10                  15

Gln Pro Lys Thr Ala Cys Thr Thr Cys Tyr Cys Lys Lys Cys Cys Phe
            20                  25                  30

His Cys Gln Val Cys Phe Thr Lys Lys Ala Leu Gly Ile Ser Tyr Gly
        35                  40                  45

Arg Lys Lys Arg Arg Gln Arg Arg Ala Pro Glu Asp Ser Gln Thr
    50                  55                  60

His Gln Val Ser Leu Pro Lys Gln Pro Ala Pro Gln Phe Arg Gly Asp
65                  70                  75                  80

Pro Thr Gly Pro Lys Glu Ser Lys Lys Lys Val Glu Arg Glu Thr Glu
                85                  90                  95

Thr His Pro Val Asp
            100

<210> SEQ ID NO 62
<211> LENGTH: 101
<212> TYPE: PRT
<213> ORGANISM: human immunodeficiency virus

<400> SEQUENCE: 62

Met Asp Pro Val Asp Pro Arg Leu Glu Pro Trp Lys His Pro Gly Ser
 1               5                  10                  15

Gln Pro Lys Ala Ala Cys Thr Ser Cys Tyr Cys Lys Lys Cys Cys Phe
            20                  25                  30

His Cys Gln Val Cys Phe Thr Thr Lys Gly Leu Gly Ile Ser Tyr Gly
        35                  40                  45

Arg Lys Lys Arg Arg Gln Arg Arg Ala Pro Gln Asp Ser Gln Thr
    50                  55                  60

His Gln Val Ser Leu Pro Lys Gln Pro Ala Ser Gln Ala Arg Gly Asp
65                  70                  75                  80

Pro Thr Gly Pro Lys Glu Ser Lys Lys Lys Val Glu Arg Glu Thr Glu
                85                  90                  95

Thr Asp Pro Val Asp
            100

<210> SEQ ID NO 63
<211> LENGTH: 101
<212> TYPE: PRT
<213> ORGANISM: human immunodeficiency virus

<400> SEQUENCE: 63
```

```
Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
                20                  25                  30

His Cys Gln Val Cys Phe Ile Thr Lys Gly Leu Gly Ile Ser Tyr Gly
            35                  40                  45

Arg Lys Lys Arg Gln Arg Arg Ala Pro Asp Ser Glu Val
        50                  55                  60

His Gln Val Ser Leu Pro Lys Gln Pro Ala Ser Gln Pro Gln Gly Asp
65                  70                  75                  80

Pro Thr Gly Pro Lys Glu Ser Lys Lys Lys Val Glu Arg Glu Thr Glu
                85                  90                  95

Thr Asp Pro Val His
            100

<210> SEQ ID NO 64
<211> LENGTH: 101
<212> TYPE: PRT
<213> ORGANISM: human immunodeficiency virus

<400> SEQUENCE: 64

Met Glu Pro Val Asp Pro Ser Leu Glu Pro Trp Lys His Pro Gly Ser
1               5                   10                  15

Gln Pro Lys Thr Ala Cys Thr Asn Cys Tyr Cys Lys Lys Cys Cys Leu
                20                  25                  30

His Cys Gln Val Cys Phe Thr Thr Lys Gly Leu Gly Ile Ser Tyr Gly
            35                  40                  45

Arg Lys Lys Arg Arg Gln Arg Arg Pro Pro Gln Asp Ser Gln Thr
        50                  55                  60

His Gln Val Ser Leu Pro Lys Gln Pro Ser Ser Gln Arg Gly Asp
65                  70                  75                  80

Pro Thr Gly Pro Lys Glu Ser Lys Lys Lys Val Glu Arg Glu Thr Glu
                85                  90                  95

Thr Asp Pro Asp Asn
            100

<210> SEQ ID NO 65
<211> LENGTH: 101
<212> TYPE: PRT
<213> ORGANISM: Artificial Sequence
<220> FEATURE:
<223> OTHER INFORMATION: consensus sequence

<400> SEQUENCE: 65

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
                20                  25                  30

His Cys Gln Val Cys Phe Ile Thr Lys Ala Leu Gly Ile Ser Tyr Gly
            35                  40                  45

Arg Lys Lys Arg Gln Arg Arg Pro Pro Gln Gly Ser Gln Thr
        50                  55                  60

His Gln Val Ser Leu Ser Lys Gln Pro Thr Ser Gln Ser Arg Gly Asp
65                  70                  75                  80
```

```
Pro Thr Gly Pro Lys Glu Ser Lys Lys Lys Val Glu Arg Glu Thr Glu
                85                  90                  95
Thr Asp Pro Phe Asp
            100
```